(12) United States Patent
Bohman et al.

(10) Patent No.: US 10,980,905 B2
(45) Date of Patent: Apr. 20, 2021

(54) OZONE SANITIZING SYSTEM AND METHOD

(71) Applicant: SLEEP 8, INC., Brentwood, TN (US)

(72) Inventors: David Paul Bohman, Nashville, TN (US); Richardson Marshall Roberts, Nashville, TN (US); Robert Emmet Seibels, IV, Nashville, TN (US); Jordan Chase Soblick, Delray Beach, FL (US); Eugene Frederick Durham, Nashville, TN (US)

(73) Assignee: SLEEP 8, INC., Brentwood, TN (US)

( * ) Notice: Subject to any disclaimer, the term of this patent is extended or adjusted under 35 U.S.C. 154(b) by 0 days.

(21) Appl. No.: 16/855,501

(22) Filed: Apr. 22, 2020

(65) Prior Publication Data

US 2020/0246498 A1 Aug. 6, 2020

Related U.S. Application Data

(63) Continuation of application No. 16/454,946, filed on Jun. 27, 2019, now Pat. No. 10,660,980.

(60) Provisional application No. 62/692,316, filed on Jun. 29, 2018, provisional application No. 62/756,338, filed on Nov. 6, 2018.

(51) Int. Cl.
*A61L 2/20* (2006.01)
*C01B 13/11* (2006.01)

(52) U.S. Cl.
CPC .............. *A61L 2/202* (2013.01); *C01B 13/11* (2013.01); *A61L 2202/11* (2013.01); *A61L 2202/122* (2013.01); *A61L 2202/123* (2013.01); *A61L 2202/15* (2013.01); *A61L 2202/24* (2013.01)

(58) Field of Classification Search
CPC ...... A61L 2/202; A61L 2/20; A61L 2202/122; A61L 2202/123; C01B 13/11
See application file for complete search history.

(56) References Cited

U.S. PATENT DOCUMENTS

| 5,120,512 | A | 6/1992 | Masuda |
| 6,134,806 | A * | 10/2000 | Dhaemers ............... F26B 21/00 34/404 |
| 6,503,547 | B1 | 1/2003 | Lima |
| 2003/0152480 | A1 | 8/2003 | Sham |
| 2005/0158221 | A1 | 7/2005 | McNulty |
| 2009/0311138 | A1 | 12/2009 | Klaptchuk |
| 2010/0196194 | A1 | 8/2010 | Voeten et al. |

(Continued)

OTHER PUBLICATIONS

International Search Report and Written Opinion, dated Oct. 4, 2019, for International Application No. PCT/US2019/039448 filed on Jun. 27, 2019, from International Search Authority, pp. 1-15.

*Primary Examiner* — Sean E Conley
(74) *Attorney, Agent, or Firm* — Bass, Berry & Sims, PLC

(57) ABSTRACT

The present disclosure generally relates to an ozone sanitizing system and method. In one embodiment, a system for sanitizing various objects using ozone gas is disclosed. The system comprises an ozone generating device configured generate ozone gas for sanitizing one or more objects, and a vessel configured to couple with the ozone generating device for receiving the ozone gas to sanitize the one or more objects stored inside the vessel during an ozone sanitizing cycle. The system is configured to recirculate at least a gas mixture generated during the ozone sanitizing cycle to increase an ozone concentration inside the vessel.

10 Claims, 14 Drawing Sheets

(56) References Cited

U.S. PATENT DOCUMENTS

2016/0235874 A1 8/2016 Blakeman et al.
2017/0197003 A1 7/2017 Taggart
2018/0207307 A1 7/2018 Schwartz et al.

* cited by examiner

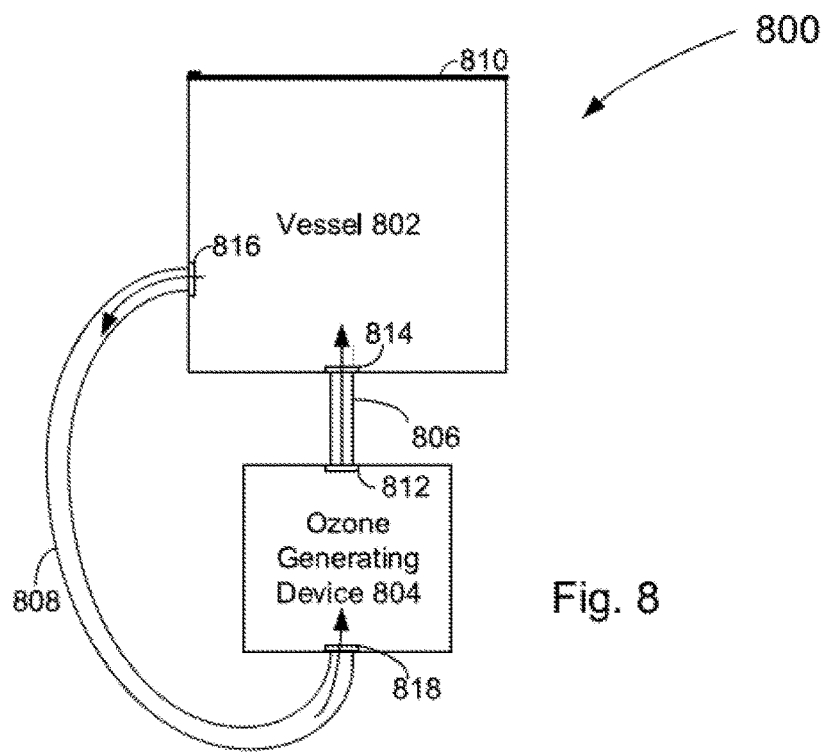
Fig. 8
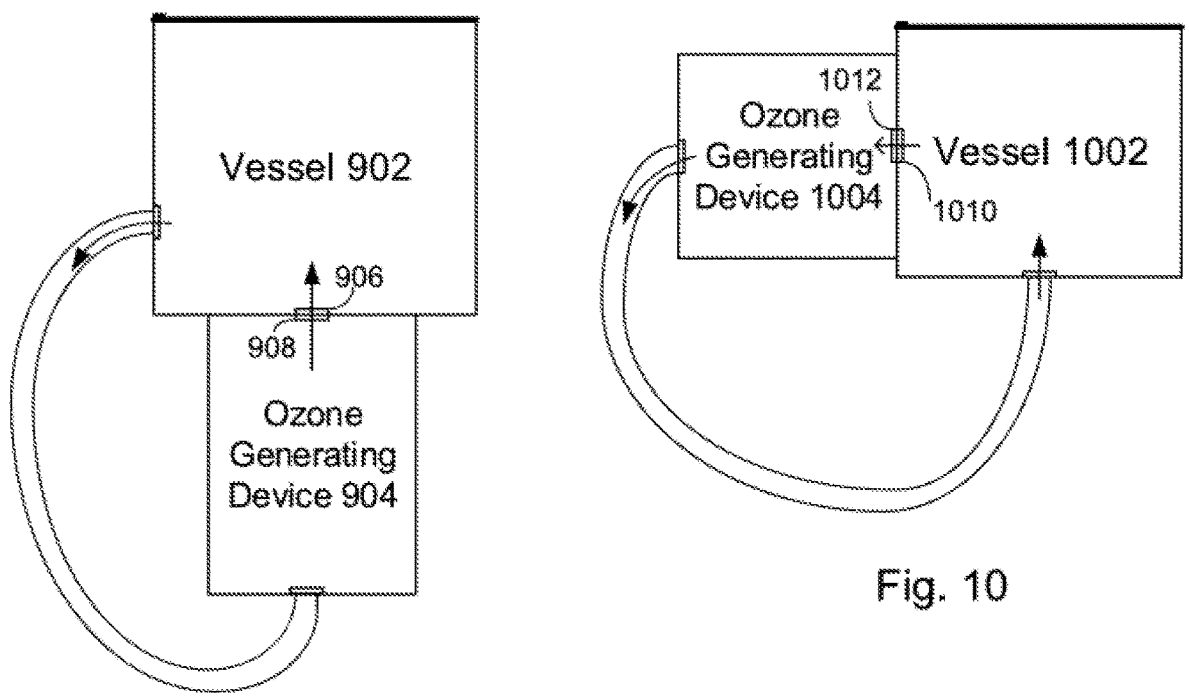
Fig. 9
Fig. 10

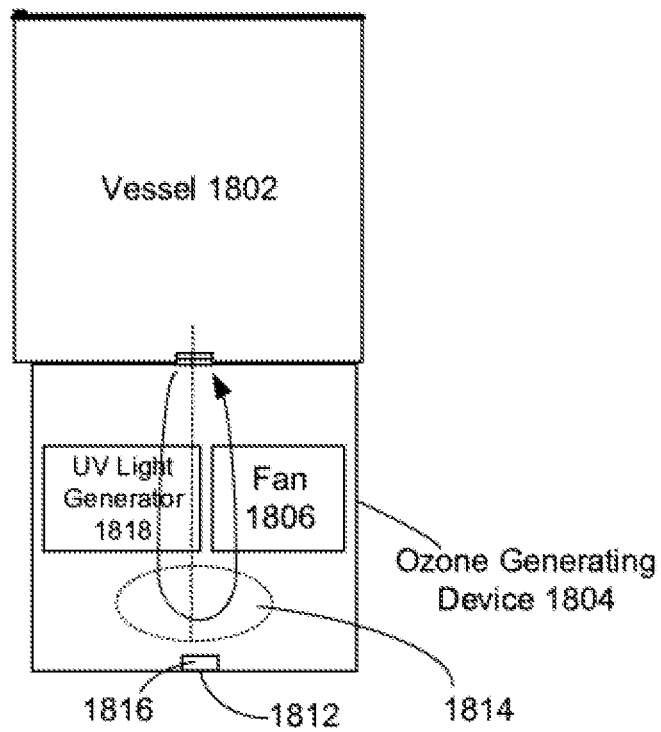
Fig. 18 (purge through UV treatment region)
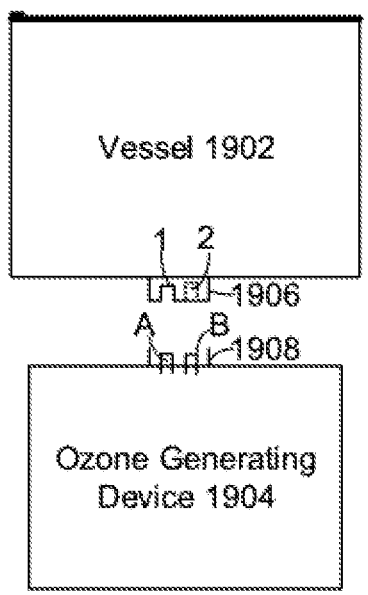
Fig. 19

OZONE SANITIZING SYSTEM AND METHOD

CROSS REFERENCE TO RELATED APPLICATIONS

This application is a continuation of U.S. patent application Ser. No. 16/454,946, filed Jun. 27, 2019, which claims the benefit of and priority to U.S. provisional patent application No. 62/692,316, filed Jun. 29, 2018, and U.S. provisional patent application No. 62/756,338, filed Nov. 6, 2018, the disclosure of each is incorporated by references in its entirety.

FIELD OF TECHNOLOGY

The present disclosure generally relates to an ozone sanitizing system and method for disinfecting various devices and objects placed in a sanitizing vessel using ozone gas, and more particularly relates to coupling an ozone generating, device with the sanitizing vessel in different configurations, such that a gas mixture generated during a sanitizing cycle is recirculated to increase an ozone concentration inside the sanitizing vessel.

BACKGROUND

Ozone ($O_3$), a naturally occurring gas in the upper atmosphere, has long been recognized as an effective and powerful disinfectant. As a highly reactive gas composed of three oxygen atoms, ozone gas rapidly oxidizes bacteria and viruses it comes in contact using the third, loosely-bonded oxygen atom, then reverts safely back into oxygen ($O_2$), making it one of the most environmentally friendly cleaning methods available. In its gaseous form, ozone flows over surfaces, travels deep into holes, surfaces, fabrics and crevices, and disperses thoroughly into the ambient environment. Ozone cleaning and sterilization offers a number of advantages: it produces no toxic waste, does not require the handling of dangerous gas cylinders, and generally poses no threat to the environment or the user's health. Ozone can also be used to eliminate or reduce unpleasant odors on or within the same types of materials by oxidizing the compounds that produce those odors.

As a result, ozone gas may be used in mold remediation, air sanitizing, water purification, commercial laundering, and equipment sterilization such as medical devices sterilization. It is known that all devices, instruments and accessories used for medical purposes (collectively "medical devices") require varying degrees of cleaning, disinfection and sterilization before these devices can be reused on the same or different patient. Medical devices with surface irregularity or complexity, such as hoses and tubes, are difficult to completely clean, disinfect and sterilize. These hard-to-reach places are particularly prone to bacteria, mold and microorganism growth and accumulation, as medical devices often come into contact with various body fluids, water and chemical agents. To avoid serious health risks, hospitals, surgical centers, medical test centers, sleep centers, nursing homes and the like often opt for single-use or disposable medical devices, resulting in a significant expense with adverse environmental impact. For reusable medical devices, reprocessing is labor-intensive, time-consuming, expensive, and often requires a specific reprocessing regimen. Preferably, after each use, reusable medical devices and any residual contaminants are kept moist in order to make the cleaning process easier and more effective. Thorough manual and mechanical cleaning is needed for all reusable medical devices prior to disinfection or sterilization. This step requires the use of proper cleaning solutions (e.g., water, detergent, surfactants, buffers, chelating agents, or enzymes) and processes to assure that all surfaces, internal and external, are completely free of bio-burden. Finally, the devices should be thoroughly rinsed to remove all residual bio-burden and detergent, and then dried properly.

A medical device may be classified in terms of potential risk of infection towards a patient or between patients if the medical device is reused. Examples of critical medical devices may include surgical instruments, irrigation systems for sterile instruments in sterile tissues, endoscopes and endoscopic biopsy accessories. These critical devices are introduced directly in the bloodstream or may contact normally sterile tissue and have a possibility of microbial transmission if the medical devices are not sterile, thus strict cleaning and sterilization thereof is required. Semi-critical medical devices may be categorized as devices that contact mucous membranes, for example, duodenoscopes, endotracheal tubes, bronchosopes, laryngosopes, blades and other respiratory equipment, esophageal manometry probes, diaphragm fitting rings and gastrointestinal endoscopes. Disinfection and/or sterilization are required before such a semi-critical medical device can be reused. Non-critical medical devices may have surface contacts with a patient's skin but do not penetrate the skin. Non-critical devices also include devices that may become contaminated with microorganisms and organic soil during patient care, such as infusion pumps, and ventilators. For example, continuous positive airway pressure (CPAP) devices are prone to bacterial build-up because of humidified air and contact with a patient's mouth. Many of the devices described above include passageways that are difficult to clean, disinfect and sterilize, such as endoscopes, probes, ventilators and specifically CPAP device parts, CPAP hoses, and CPAP facemasks.

It is thus desirable to provide ozone sanitizing system and method for cleaning, disinfecting and sterilizing various objects such as medical device components and parts that come in different shapes and sizes.

It is known that ozone concentration is important to the killing of pathogens on an item being sanitized. However, when an ozone gas generator is used to generate ozone gas with a relatively high concentration, it may require more power to be provided to the ozone gas generator. For a rechargeable or portable sanitizing system using ozone gas, a relatively high ozone concentration output may require a battery with high capacity for a portable ozone gas generator or a limited number of ozone cleaning cycles. Generally speaking, the bigger the battery, the higher the capacity of the battery and a heavier and bulkier design for the ozone gas generator.

In addition, where the ozone/air mixture used for sanitizing is continuously injected into a vessel with an exhaust port during the sanitizing cycle, the ozone in the ozone/air mixture discharged from, the exhaust port may need to be neutralized. This can reduce the life cycle of the neutralizing material versus a system where only the ozone remaining after the sanitizing cycle is neutralized. Moreover, it may be desirable to rapidly increase the concentration of ozone in the vessel to reduce the time required for sanitation. If the air/ozone mixture is discharged through an exhaust port, the amount of ozone being discharged is subtracted from the ozone in the sanitizing vessel. By recirculating the air/ozone mixture in the vessel such that no ozone is discharged from the vessel during the sanitizing cycle, the concentration of ozone increases more rapidly.

It is thus desirable to provide an ozone recirculation system and method for cleaning, disinfecting and sterilizing various objects with increased ozone concentration without requiring an ozone gas generator having a higher output or requiring the underlying system to continuously neutralize ozone gas that is discharged during the sanitizing cycle. To improve the efficacy of an ozone sanitizing system, it is also desirable to inflate a vessel made of a flexible material and fully expose surfaces of objects stored therein for ozone treatment. Further, it is desirable for an ozone sanitizing system to automatically identify the size of the vessel and determine an appropriate ozone treatment duration.

SUMMARY

The present disclosure discloses, among other features, a system for sanitizing various objects using ozone gas. The system may comprise an ozone generating device configured to generate ozone gas for sanitizing one or more objects; and a vessel configured to couple with the ozone generating device for receiving the ozone gas to sanitize the one or more objects stored inside the vessel during an ozone sanitizing cycle. The system is configured to recirculate at least a gas mixture generated during the ozone sanitizing cycle to increase an ozone concentration inside the vessel.

In one aspect, the system may comprise a first connecting means for coupling a first end of the ozone generating device and a first end of the vessel such that the ozone gas generated by the ozone generating device is directed into the vessel through the first connecting means; and a second connecting means for coupling a second end of the ozone generating device and a second end of the vessel such that the gas mixture inside the vessel during the ozone sanitizing cycle is directed through the second connecting means into the ozone generating device for additional ozone generation to be delivered via the first connecting means into the vessel.

When a first end of the ozone generating device and a first end of the vessel are configured to couple with each other directly without using any connecting hose, the system may comprise a connecting means for coupling a second end of the ozone generating device and a second end of the vessel such that the gas mixture generated during the ozone sanitizing cycle is directed through the connecting means between the vessel and the ozone generating device for additional ozone generation to be delivered into the vessel.

In yet another aspect, an outlet port of the ozone generating device and an inlet port of the vessel may be configured to couple with each other directly without using any connecting hose during the ozone sanitizing cycle. The outlet port and the inlet port may be configured to form: a first gas conduit for delivering the ozone gas generated by the ozone generating device into the vessel, and a second gas conduit for directing the gas mixture inside the vessel during the ozone sanitizing cycle into the ozone generating device for additional ozone generation to be delivered through the first gas conduit into the vessel.

In another aspect, an outlet port of the ozone generating device and an inlet port of the vessel may be configured to couple with each other directly without using any connecting hose, such that the ozone gas generated by the ozone generating device is directed into the vessel during the ozone sanitizing cycle. An inlet port of the ozone generating device and an outlet port of the vessel may be configured to couple with each other directly without using any connecting hose, such that the gas mixture inside the vessel is directed into the ozone generating device for additional ozone generation to be delivered through the outlet port of the ozone generating device into the interior of the vessel.

The ozone generating device may be configured to use a corona discharge to generate the ozone gas and may include at least one valve to inflate the vessel prior to the ozone sanitizing cycle. The valve may detect an air pressure difference between a surrounding environment of the system and an interior of the system, and close or open in response to detecting the air pressure difference such that at least the gas mixture is recirculated.

In one aspect, the vessel of the system may comprise: a first end having a resealable locking means for providing access to an interior of the vessel in an open position and for preventing ozone gas leakage from the vessel in a closed position; and a second end having a portal implemented thereon.

The portal may include a first port for connecting with one object stored inside the vessel, a second port for connecting with an ozone gas release port of the ozone generating device, and a connector portion affixing the portal to the second end of the vessel and connecting the first and second ports. The first port, the second port, and the connector portion may be concentrically aligned along a longitudinal axis, and the first and second ports may have different cross sectional profiles. Moreover, the second port may mate with a matching port implemented around the ozone gas release port of the ozone generating device. The ozone generating device may further comprise a safety switch configured to prevent the ozone generating device from generating the ozone gas in response to detecting that the second port is improperly connected to the matching port.

In yet another aspect, the system may be configured to purge the ozone gas inside the ozone generating device and the vessel at the end of the ozone sanitizing cycle to prevent the ozone gas from being released into the surrounding area when the vessel is opened for retrieval of the one or more objects therein.

The ozone generating device may be configured to have at least one fan with at least two different speeds. The fan may be configured to operate with a first speed during the ozone sanitizing cycle, and operate with a second speed at the end of the ozone sanitizing cycle, the second speed being higher than the first speed. At least one of the ozone generating device and the vessel may have a discharge port coupled with an ozone gas neutralizing device. The system may further comprise a pressure sensitive valve installed on the discharge port, and the valve may be configured to: close in response to detecting a lower pressure in the vessel and the fan is operating with the first speed, and open in response to detecting a greater pressure in the vessel and the fan is operating with the second speed.

In addition, the ozone generating device may be configured to internally create an air pressure difference region along an air recirculation path, wherein the air pressure difference region is configured to have a fluid communication with a surrounding environment of the ozone generating device via inlet and outlet ports of the ozone generating device.

In another aspect, the system may be configured to identify a size of the vessel and determine an ozone treatment duration based at least on the size of the vessel.

The present disclosure also discloses, among other features, a method for sanitizing various objects using ozone gas. The method may comprise: generating ozone gas using an ozone generating device: coupling a vessel with the ozone generating device for receiving the ozone gas to sanitize one or more objects stored inside the vessel during an ozone sanitizing cycle; and recirculating at least a gas mixture generated during the ozone sanitizing cycle to increase an ozone concentration inside the vessel.

In one aspect, the method may comprise coupling a first end of the ozone generating device and a first end of the vessel using a first connecting means, such that the ozone gas generated by the ozone generating device is directed into the vessel through the first connecting means; and coupling a second end of the ozone generating device and a second end of the vessel using a second connecting means, such that the gas mixture inside the vessel during the ozone sanitizing cycle is directed through the second connecting means into the ozone generating device for additional ozone generation to be delivered via the first connecting, means into the vessel.

In another aspect, the method may comprise coupling a first end of the ozone generating device and a first end of the vessel with each other directly without using any connecting hose; and coupling a second end of the ozone generating device and a second end of the vessel using a connecting means, such that the gas mixture generated during the ozone sanitizing cycle is directed through the connecting means between the vessel and the ozone generating device for additional ozone generation to be delivered into the vessel.

In yet another aspect, the method may comprise coupling an outlet port of the ozone generating device and an inlet port of the vessel with each other directly without using any connecting hose during the ozone sanitizing cycle; forming a first gas conduit through the outlet port and the inlet port for delivering the ozone gas generated by the ozone generating device into the vessel; and forming a second gas conduit through the outlet port and the inlet port for directing the gas mixture inside the vessel during the ozone sanitizing cycle through the second gas conduit into the ozone generating device for additional ozone generation to be delivered into the vessel.

In another aspect, the method may comprise coupling an outlet port of the ozone generating device and an inlet port of the vessel with each other directly without using any connecting hose, such that the ozone gas generated by the ozone generating device is directed into the vessel during the ozone sanitizing cycle; and coupling an inlet port of the ozone generating device and an outlet port of the vessel with each other directly without using any connecting hose, such that the gas mixture inside the vessel is directed into the ozone generating device for additional ozone generation to be delivered through the outlet port of the ozone generating device into the vessel.

The method may further comprise installing at least one valve on the ozone generating device to inflate the vessel prior to the ozone sanitizing cycle; detecting, by the valve, an air pressure difference between a surrounding environment of the ozone generating device and the vessel and an interior of the ozone generating device and the vessel; and closing or opening, by the at least one valve, in response to detecting the air pressure difference such that at least the gas mixture is recirculated.

In yet another aspect, the method may comprise purging the ozone gas inside the ozone generating device and the vessel at the end of the ozone sanitizing cycle to prevent the ozone gas from being released into the surrounding area when the vessel is opened for retrieval of the one or more objects therein.

In addition, the method may comprise installing at least one fan with at least two different speeds within the ozone generating device, wherein the fan may operate with a first speed during the ozone sanitizing cycle, and operate with a second speed at the end of the ozone sanitizing cycle. the second speed being higher than the first speed; installing a discharge port coupled with an ozone gas neutralizing device on at least one of the ozone generating device and the vessel; and installing a pressure sensitive valve on the discharge port. The pressure sensitive valve may be configured to: close in response to detecting a lower pressure in the vessel and the fan is operating with the first speed, and open in response to detecting a greater pressure in the vessel and the fan is operating with the second speed.

Moreover, the method may comprise creating an air pressure difference region along an air recirculation path inside the ozone generating device. the air pressure difference region having a fluid communication with a surrounding environment of the ozone generating device via inlet and outlet ports of the ozone generating device. The method may also comprise identifying a size of the vessel and determining an ozone treatment duration based at least on the size of the vessel.

The above simplified summary of example aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows. To the accomplishment of the foregoing, the one or more aspects of the present disclosure include the features described and exemplary pointed out in the claims.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

FIG. 8 illustrates a first embodiment of recirculating ozone gas within an ozone sanitizing system, according to an exemplary aspect;

FIG. 9 illustrates a second embodiment of recirculating ozone gas within an ozone sanitizing system, according to an exemplary aspect;

FIG. 10 illustrates a third embodiment of recirculating ozone gas within an ozone sanitizing system, according to an exemplary aspect;

FIGS. 16-18 illustrates example implementations for purging residual ozone gas within an ozone sanitizing system at the end of an ozone sanitizing cycle, according to an exemplary aspect; and FIG. 19 illustrates an example implementation of coupling structures between a vessel and an ozone generating device of an ozone sanitizing system for identifying the size of the vessel, according to an exemplary aspect.

DETAILED DESCRIPTION

Figure 1:
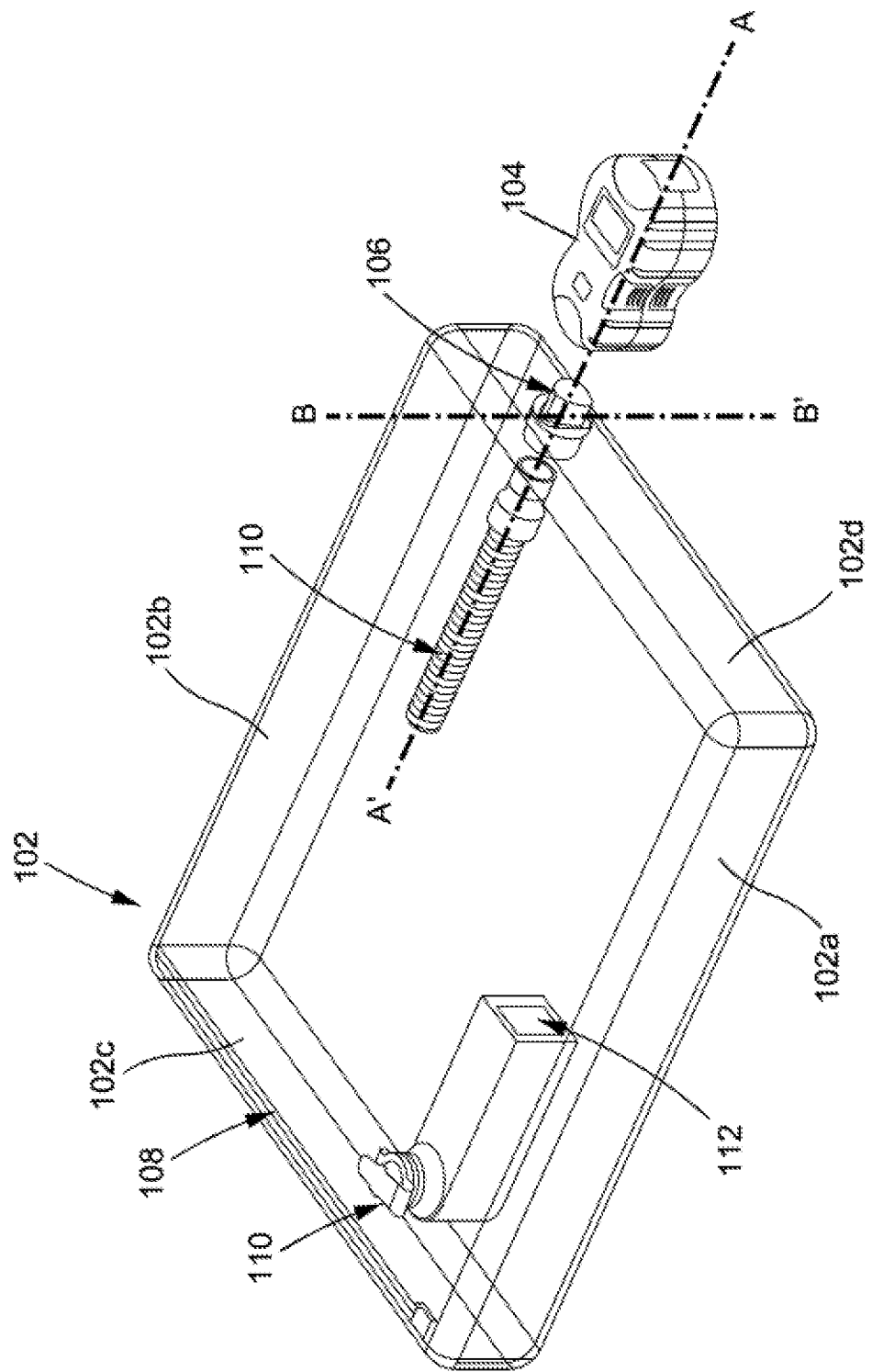
FIG. 1 illustrates a portable system for sanitizing medical devices using ozone gas, according to an exemplary aspect.

Various aspects of the disclosure will be described with reference to the drawings, wherein like reference numerals are used to refer to like elements throughout. In the following description, for purposes of explanation, numerous specific details are set forth in order to promote a thorough understanding of one or more aspects of the disclosure. It may be evident in some or all instances, however, that any aspects described below can be practiced without adopting the specific design details described below.

As discussed above, many medical devices comprise a complex geometry or features that match a patient's unique anatomy, and some may include passageways that are difficult to clean, disinfect and sterilize, such, as endoscopes, probes, ventilators and CPAP device parts, CPAP hoses, and CPAP facemasks.

It is known that CPAP therapy and devices may be useful and effective for treating obstructive sleep apnea (OSA) by providing air at a constant positive pressure to the respiratory system of a sleeping patient. OSA is a serious sleep disorder that causes a person to stop breathing during sleep. OSA occurs when the back muscles of a person's throat relax while sleeping, causing the airway to narrow, resulting in snoring. These muscles may also completely block the flow of air to the lungs. When the brain detects a lack of oxygenation, it sends an impulse to the muscles forcing them to restart the breathing process. OSA may cause fragmented sleep and low blood oxygen levels leading to high blood pressure, heart disease, stroke, diabetes, depression, and other health issues. Patients with OSA treated with CPAP may wear a facemask during sleep which is connected to a pump that forced air into the nasal passages at pressures high enough to overcome obstructions in the airway and stimulate normal breathing. The airway pressure delivered into the upper airway is continuous during inspiration and expiration.

Generally speaking, a CPAP device may include a CPAP motor, CPAP hoses and a CPAP facemask. During operation, the CPAP motor may draw in room temperature air and pressurize it for delivering a stream of pressured air through a hose to a nasal pillow or full facemask surrounding a sleeping patient's nose. Certain CPAP devices may be equipped with a small water tank that, when turned on, heats up the water to provide moisture to the pressurized air. These built-in humidifiers are ideal for people living in dry or arid climates and those that frequently wake with dry mouth, throat, or nasal cavities. Accordingly, hoses may be heated to reduce water condensation accumulation caused by the humidifiers.

Regular cleaning and disinfecting of a CPAP device is of vital importance, as moisture accumulated on various components of the device can be a breeding ground for mold, bacteria and viruses. However, such regular maintenance of a CPAP device has proven to be difficult, especially for users who are away from home or travelling.

Accordingly. there is a need for simplified, safe and effective method and system for cleaning and disinfecting various components of a CPAP device.

Referring to FIG. 1, a reusable, disposable, and flexible gusset bag 102 and a portable ozone generating device 104 may be used to sanitize various objects including components and parts of medical devices using ozone gas, according to aspects of the present application. As utilized herein, the term "flexible" may generally refers to materials that are capable of being flexed or bent, especially repeatedly, such that they are pliant and yieldable in response to externally applied forces. Accordingly, "flexible" may he substantially opposite in meaning to the terms inflexible, rigid, or unyielding. Materials and structures which are flexible, therefore, may be altered in shape and structure to accommodate external forces and to conform to the shape of objects brought into contact with them without losing their integrity.

Figure 2A:
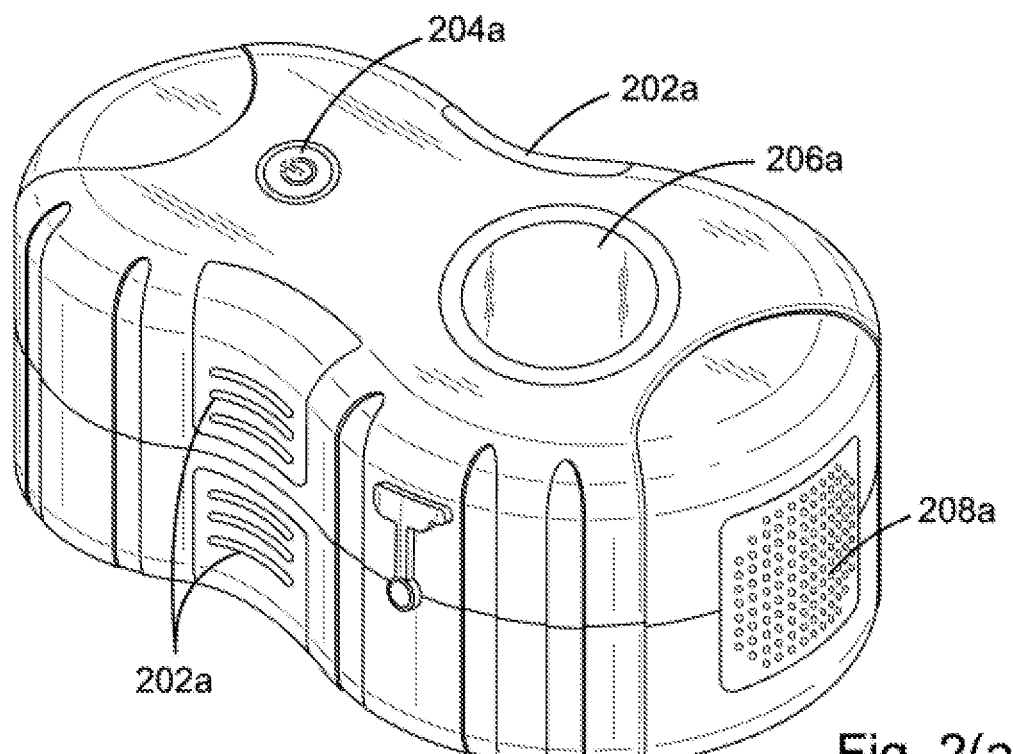
FIGS. 2(a)-2(b) illustrate two embodiments of a portable ozone generating device, according to an exemplary aspect.
Figure 2B:
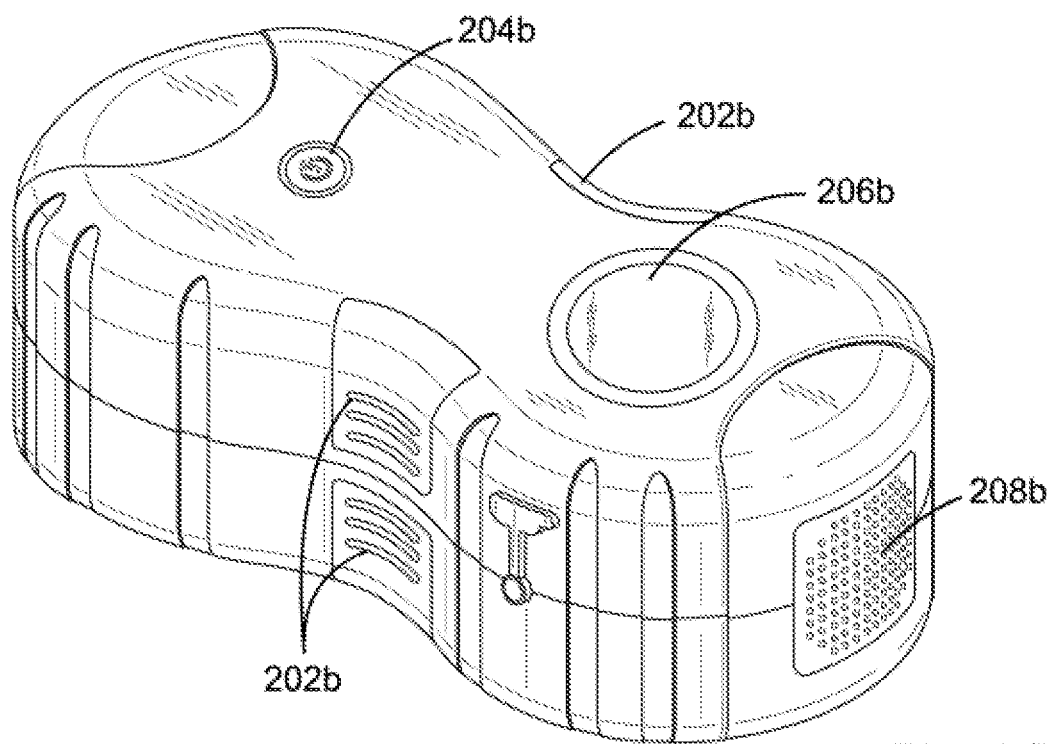

As shown in FIGS. 2(a) and 2(b), ozone generating device 104 is a compact and portable device and has an outer casing with an ozone generating system (not shown) embedded therein for generating a safe amount of ozone gas in compliance with relevant government regulations for sanitizing purposes. In one aspect, the outer casing of ozone generating device 104 may be configured to have a figure "8" shape: an asymmetrical figure "8" shape with a small circle and a big circle as shown in FIG. 2(a), or a symmetrical figure "8" shape with two identical sized circles as shown in FIG. 2(b). To provide a non-slipping grip and handling of ozone generating device 104, two pairs of ribbed thermoplastic elastomer (TPE) pads 202a, 202b may be implemented around the narrow portions where the two circles connect with each other. On the top surface of the outer casing, a power button 204a, 204b and a liquid crystal display (LCD) 206a, 206b may be implemented. As will be described fully below, a plurality of indicators and signals may be used to display the operating status of ozone generating device 104 to a user via LCD 206a, 206b. Inside the outer casing, ozone generating device 104 may include circuitry that produces ozone gas by drawing in ambient air through a fan cover 208a, 208b having a plurality of air intake openings and passing oxygen in the air through a corona discharge between two parallel or concentric electrodes separated by a dielectric. The oxygen in the air is broken down to charged oxygen atoms which recombine to form molecules of ozone that contain three atoms of oxygen. A fan and an air pump (not shown) may be located inside the outer casing near the fan cover 208a, 208b so as to actively and continuously supply and drive air through ozone generating device 104 while providing an appropriate cooling of the electrodes and distributing generated ozone gas through the other end of ozone generating device 104. In one aspect, ozone generating device 104 may include circuitry to control a motor of the fan and the air pump without generating excessive acoustic noise. For example, such circuitry may be configured to provide speed control to the motor of the fan and the air pump with several selectable impedances. These impedances, typically capacitors, may represent a series of reduced levels of smooth (not switched) power to the motor from a power source of ozone generating device 104 (e.g., battery powered or an AC power source), such that the power reduction in the motor is proportional to the series of impedances.

Through a specially designed portal 106, as shown in FIG. 1, a user may connect ozone generating device 104 with the gusset bag 102, and press the power button 204a, 204b for a short period of time (e.g., 1 second or so) to turn on the ozone generating device 104 for use. In response, the LCD 206a, 206b backlight may be turned on with a beep sound to indicate that the ozone generating device 104 is becoming operational. However, if the ozone generating device 104 improperly connects with the gusset bag 102 (e.g., detected by a safety switch 506 of FIG. 5 which will be described fully below), the LCD 206a, 206b may display an error signal (e.g., a flashing "X" symbol) in response to an attempt to turn on the ozone generating device 104. Meanwhile, a buzzer alarm of the ozone generating device 104 may last for a period of time (e.g.. up to 30 seconds) to provide an audio warning that a faulty connection may exist. The user may press the power button 204a, 204b to turn off the ozone generating device 104 and adjust the connection or alignment between the device 104 and the gusset bag 102 before restarting.

During an ozone cleaning cycle, ozone generating device 104 may be configured to deliver generated ozone gas into the interior of the bag 102 for effectively deodorizing, disinfecting, and destroying bacteria, mold, fungi, allergens, and odor-causing agents that may grow or remain inside passageways of certain medical devices, such as CPAP hose or on CPAP facemask. Once properly connected with the bag 102 and powered up, the ozone generating device 104 may initially continuously produce ozone gas for, e.g., 5 minutes. Thereafter, the ozone gas production may be reduced to 20 seconds every minute for up to 30 minutes. Audio and/or visual signals may be provided to indicate the completeness of an ozone cleaning cycle. For example, a number of beep sound (e.g., 5) and a "OK" signal may be displayed on the LCD 206a, 206b for 1 minute before the ozone generating device 104 terminates the ozone cleaning cycle and powers down. In accordance with one aspect of the disclosure, the fan and air pump may be configured to remain operational after the ozone gas production has completed for an ozone cleaning cycle, During an ozone cleaning cycle, LCD 206a. 206b may display various indicators and signals to the user regarding the operating status of ozone generating device 104. For example, a fan symbol may be configured to be flashing on LCD 206a, 206b when the fan is detected to be working properly, and an ozone blow mark may be shown when ozone generating circuitry of ozone generating device 104 runs. However, in response to detecting that ozone generating device 104 is detached from portal 106 while ozone gas is being generated, the ozone blow mark may display flashing "X" symbol and a buzzer alarm may last for up to 30 seconds to warn the user to turn off ozone generating device 104 immediately. Further, a complete ozone cleaning cycle time (e.g., 35 minutes) may be displayed to the user and it will count down every minute until ozone generating device 104 stops working. Moreover, ozone generating device 104 may be powered by alternating current (AC) power or a rechargeable battery (e.g., lithium ion battery) which may be charged whenever ozone generating device 104 is plugged into a conventional AC outlet. To indicate the charging status of the rechargeable battery of ozone generating device 104, a battery symbol may be displayed on LCD 206a, 206b. For example, a flashing battery symbol may indicate a low power reserve and the user is advised to charge ozone generating device 104, When symbol "E1" is displayed on LCD 206a, 206b, the rechargeable battery becomes drained and ozone generating device 104 stops working. The user may use a universal serial bus (USB) cable to connect a USB connection port of ozone generating device 104 and supplying power from any applicable electronic device (e.g., a computer) or a typical AC power source. In response to detecting the beginning of a battery charging process, ozone generating device 104 may generate 1 beep sound and LCD backlight may turn on with 50% brightness and a flashing battery symbol. Battery capacity may be represented with, e.g., a number of bars. In one example, a battery symbol with 4 bars may indicate the battery is fully charged with 100% capacity.

Figure 3:
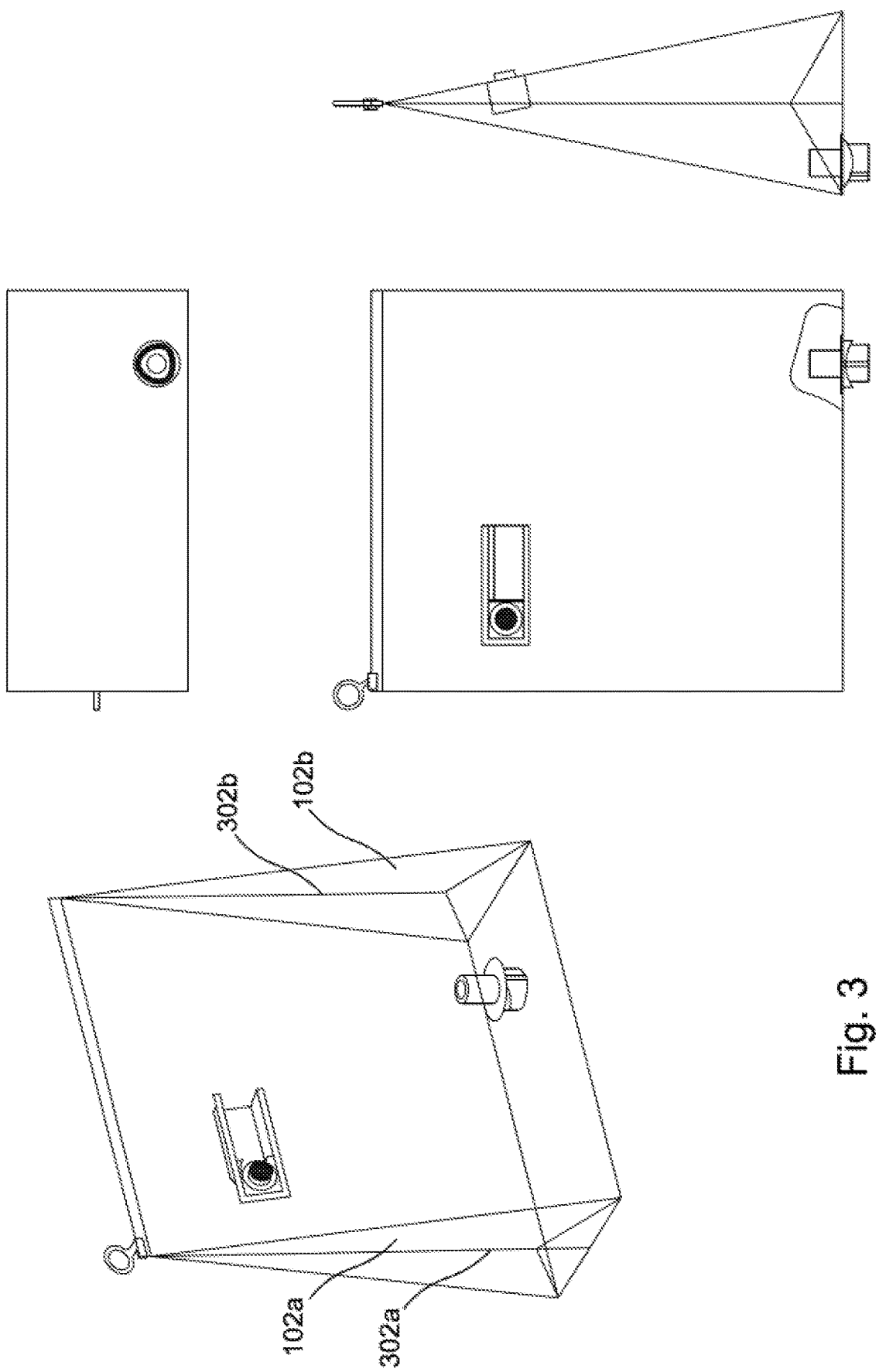
FIG. 3 illustrates a sanitizing bag design, according to an exemplary aspect.

As also shown in FIG. 1, in an aspect, the bag 102 may comprise two opposing side panels (front and rear) each made of a sheet or a multi-layered sheet of, e.g., polymerizing vinyl chloride (PVC) that may be transparent, opaque or colored. Although generally rectangular in shape as shown, either or both side panels of the bag 102 may be any conceivably useful shape such as substantially round, oval, square or rectangular shape or any practical variation of these shapes that one might design. Both side panels, in collapsed condition, may be flattened upon each other and connected along their edges via, e.g., side walls 102a-102d. For example, as shown in FIG. 1, two longitudinal parallel side walls 102a and 102b may define the length or depth of the bag 102. In an alternative compact bag design. as shown in FIG. 3, each side walls 102a and 102b may also have opposed gusseted side walls collapsible against one another along a central fold line 302a, 302, respectively.

On the shorter side of the bag 102, a top end 102c may include a resealable locking means 108 for providing access to the interior of the bag 102 in an open position and preventing ozone gas leakage in a closed position. The locking means 108 may include, e.g., a zipper or an interlocking rib-type seal, or other closure means such as plastic or paper-clad-wire ties that have strong resistance to oxidization and corrosion. For example, as shown in FIG. 3, the resealable locking means 102 may include a double zipper lock. Opposing the top end 102c, a bottom end 102d of the bag 102 may have the portal 106 formed thereon.

It should be appreciated that various suitable designs of the bag 102 may be contemplated. For example, side walls 102a-102d may be removed such that the two longitudinal parallel edges of the bag 102 may join each other directly via anti-leak seams, and the resealable locking means 108 may repeatedly and nondestructively seal the two side panels together to define a bag interior in the closed position during use. Alternatively, the bottom end 102d of the bag 102 may be reinforced (e.g., with increased thickness or use tear resistance plastic film or sheet, or a combination thereof) to better withstand the repeated dissemble and assemble forces applied on the portal 106.

The specially designed portal 106 may be a connector unit between ozone generating device 104 and a pipeline portion 110 of certain CPAP components (e.g., CPAP facemask, hoses, or tubes) that are placed inside the bag 102 for sanitizing purposes. As illustrated, during operation, the portal 106 connects the pipeline portion 110 and the ozone gas release port of the ozone generating device 104 along an axis AA', thereby forming a conduit through which generated ozone gas may flow from ozone generating device 104 into the interior of the sealed bag 102. The specially designed portal 106 may be positioned anywhere on the bag 102.

According to one aspect of the present application, referring to FIGS. 4(a)-4(d), the portal 106 may comprise at least three parts that are concentrically aligned along the axis AA': a first port 402 for either connecting with a medical device, e.g., a CPAP tube, placed inside the bag 102 or simply directing ozone gas into the bag 102; a second port 404 protruding at the base end 102d of the bag 102 for connecting with the ozone generating device 104 and receiving ozone gas therefrom; and a connector portion 406 for securely affixing the portal 106 onto the bag 102, e.g., at bottom end 102d, and connecting the first port 402 and the second port 404.

Figure 4A:
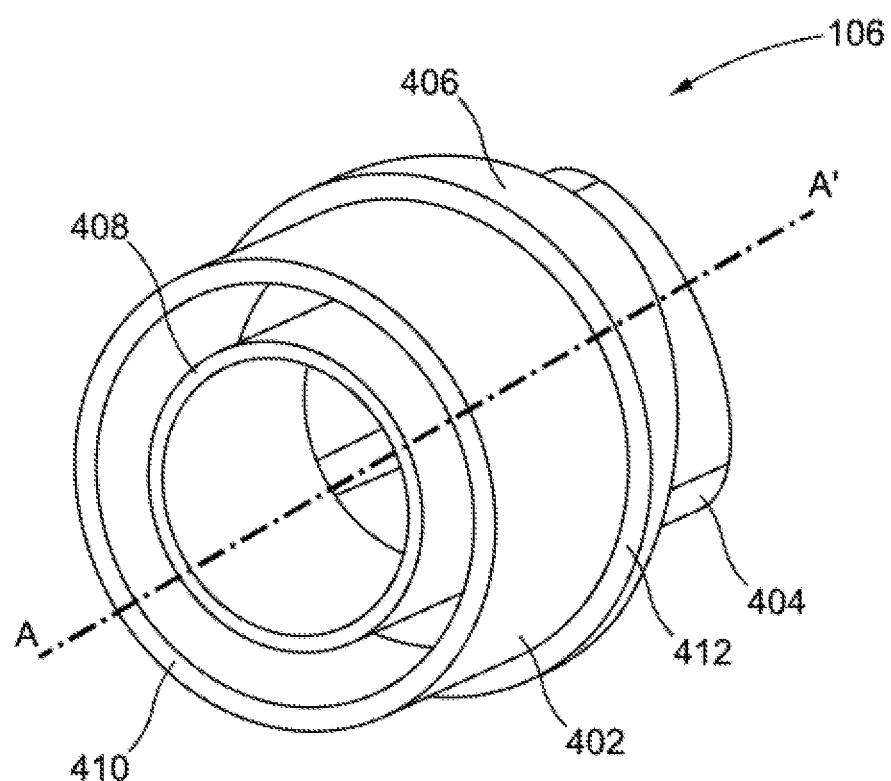
FIGS. 4(a)-4(d) illustrate various designs of a gas portal implemented on a sanitizing bag, according to an exemplary aspect.

Referring to FIG. 4(a), the first port 402 may comprise a doubled walled pipe structure with an inner flow pipe 408 concentrically encased within an outer sleeve pipe 410 with annulus space therebetween. During operation, ozone gas flows within the inner flow pipe 408 which may he connected with a medical device, e.g., the pipeline portion 110 of a standard CPAP hose, inside the sealed bag 102, as shown in FIG. 1. The outer sleeve pipe 410 may provide additional mechanical strength to keep the inner flow pipe 408 in place where thermal expansion and contraction may be present. Generally, located in the annular space formed between the external wall of the inner flow pipe 408 and the internal wall of the outer sleeve pipe 410 is insulation medium such as air or certain insulation materials. As ozone gas is a strong oxidant that may gradually erode the inner flow pipe 408 which is also subjected to repeated physical assemble and disassemble, the outer sleeve pipe 410 may provide the inner flow pipe 408 with greater resistance to corrosion and protection against external pressure.

Generally speaking, a standard CPAP hose has a smooth interior with a diameter of 19 min and ribbed outer surface, and is usually equipped with a 22 mm connection cuff which is a detachable end part for connecting the CPAP hose to a CPAP machine, a stand-alone humidifier or a CPAP facemask. Such connection cuff typically features a circular cross section and measures 22 mm in diameter. As shown in FIG. 4(c), according to an aspect of the present disclosure, the diameter of the inner flow pipe 408 of the port 402 may range from 19.6 mm to 22 mm in order to coaxially receive and tightly engage either an end portion (e.g.. 19 mm or so) of a standard CPAP hose directly or a connection cuff of the hose, while limiting excessive longitudinal and rotation movement when ozone gas flows through the port 402 into the bag 102.

Figure 4B:
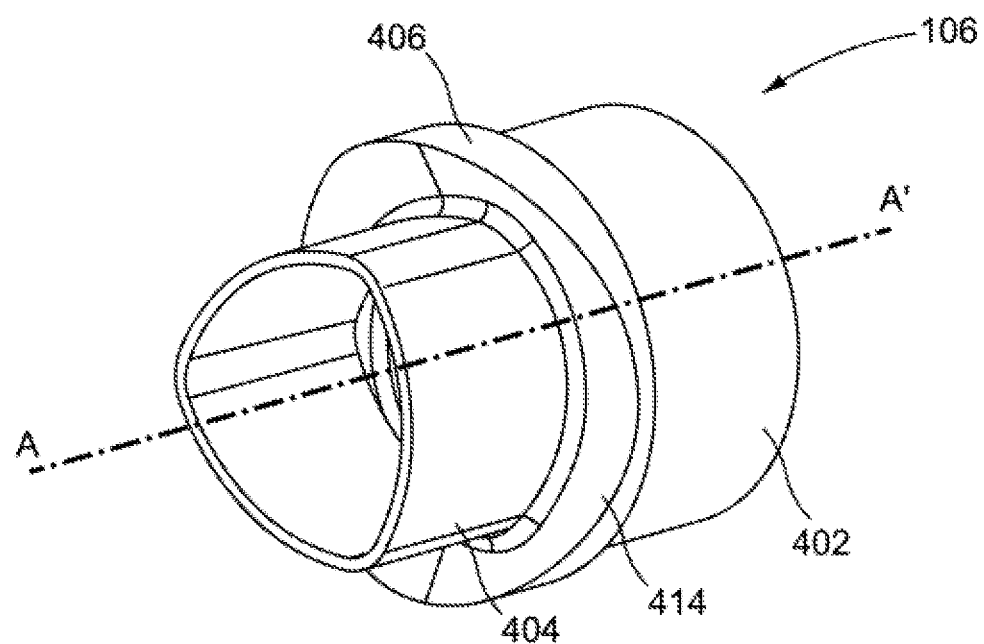
Figure 4C:
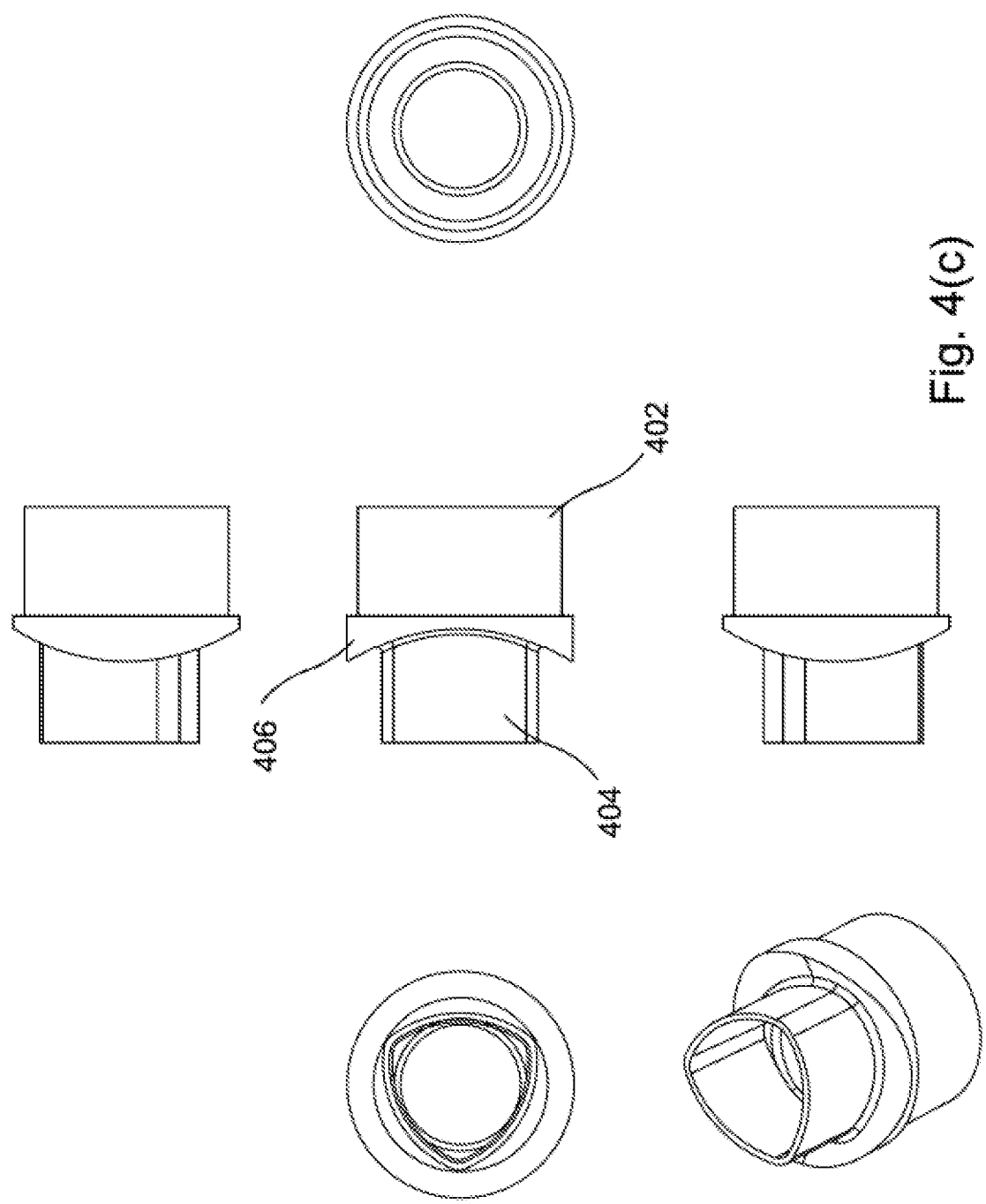

Referring to FIG. 4(b), the cross-sectional profile of the second port 404 may be different than that of the first port 402, according to aspects of the present application. That is, although the cross section of the first port 402 may be generally circular for the ease of connecting with CPAP hoses and medical device connectors that have similar cross sections, the second port 404 may be configured to have a different symmetric or asymmetric cross-sectional shape. For example, a substantially triangular profile of the second port 404, as shown in FIGS. 4(a)-4(d), may uniquely mate with a matching port 502 implemented around an ozone gas release port 504 of the ozone generating device 500, as shown in FIG. 5, thereby preventing a user from misusing the ozone gas generating device 500 for inappropriate purposes or applications. For cross-sections having corners (such as square, rectangular, or polygonal cross-sections), it may be preferable to have rounded outer surfaces on those corners to reduce stress and wear on the port 404 thereby extending the life of the portal 106. A safety switch 506 may also be built into the port receiving end of the ozone generating device 500 to prevent the ozone generating device 500 from beginning an ozone cleaning cycle (i.e., producing ozone) unless the safety switch is configured to detect a valid connection with the portal 106. As brief exposure to ozone at concentrations over a few tenths of a part per million may cause discomfort, such port design increases safety and prevents an improper connection with the ozone generating device 104.

The portal 106 may be fixedly attached and secured to the bag 102, e.g bottom end 102d of the bag 102, via the connector portion 406 which may be integrally formed onto the bag 102 by e.g., blow molding technique or manufactured separately and subsequently sealed onto the bag 102 using techniques known in the art (e.g, glues, welding. or thermal sealing). The connector portion 406 may have a flat end 412 connected with the first port 402 and a saddle shaped end 414 connected with the second port 404. In an example embodiment, as shown in FIG. 4(c), the connector portion 406 may have an outer diameter of 33.5 mm, a width of 7.2 mm measured at the widest part, and a width of 2 mm measured at the narrowest part to accommodate a range of thicknesses the bag panel may use. The inner diameter of the connector portion 406 may be dimensioned (e.g., 22 mm) to maintain a substantially uniform cross sectional area (e.g., a circular area of at least 22 mm) along the entire portal length and through each connecting point, so as to minimize a flow disruption or turbulence in the ozone gas flow passing therethrough. As the bag 102 is designed to be used multiple times with ozone gas inflates and stretches the bag during each use, the connector portion 406 should be made of materials that are durable yet flexible with sufficient elastic memory to quickly reposition itself on the bottom end of the bag 102 in order to maintain air-tight sealing even after repeated insertion and removal of various components on both ports 402 and 404. The saddle shaped end 414 of the connector portion 406 may include a pair of convex surfaces symmetrically positioned along an axis BB' as shown in FIG. 1 that is perpendicular to the longitudinal axis AA', thereby creating a concave central section between the convex surfaces to accommodate a safety switch 506 of the ozone generating device 500 of FIG. 5. In addition, more grip area of the portal 106 and a larger field of view of the connection between the portal 106 and the ozone generating device 104 may be achieved due to such concavity on the saddle shaped end 414, thereby facilitating a more effective visual inspection and quick user response to, e.g., accidental disengagement between matching ports 404 and 502 during use.

Figure 4D:
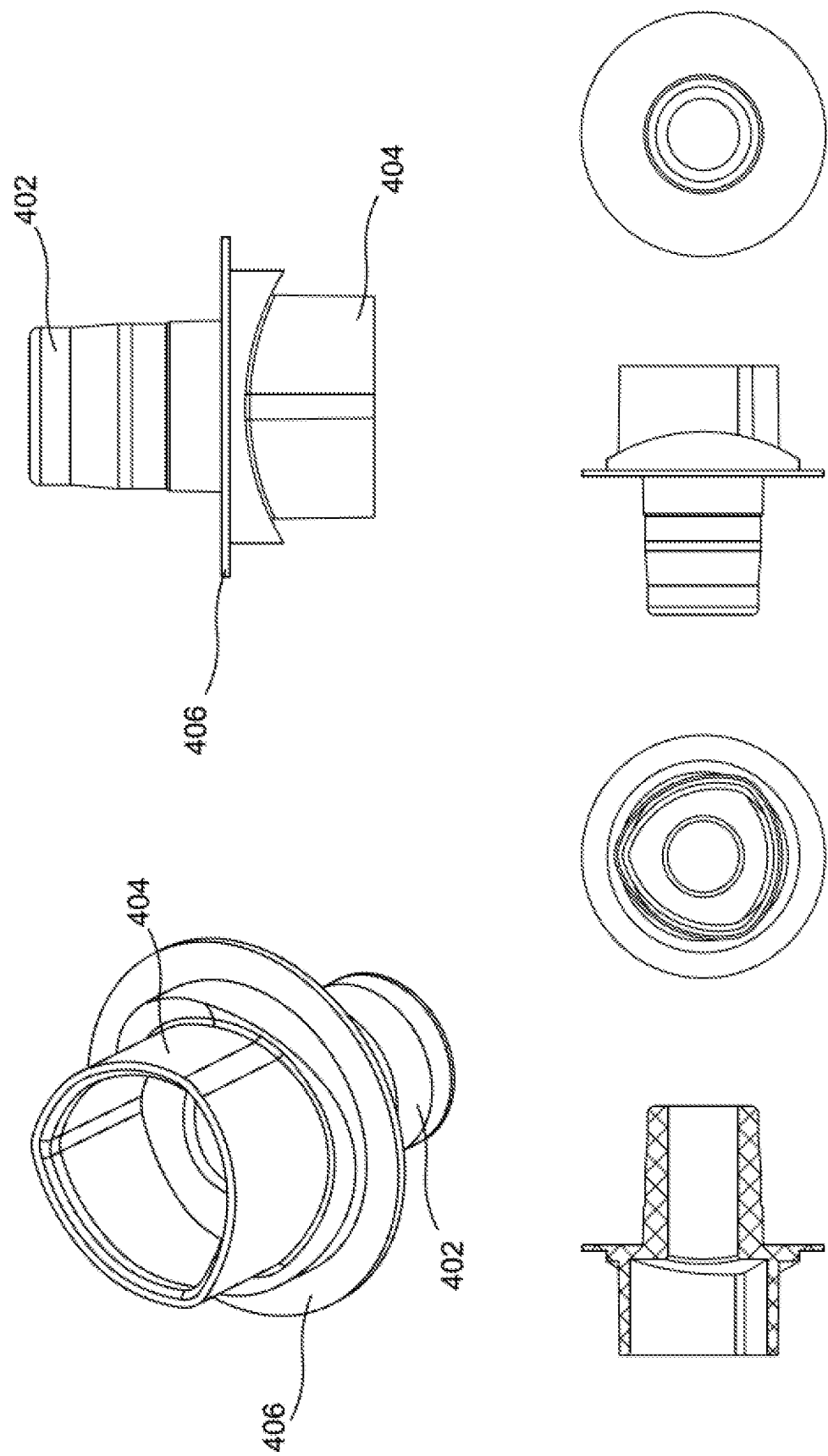
Figure 5:
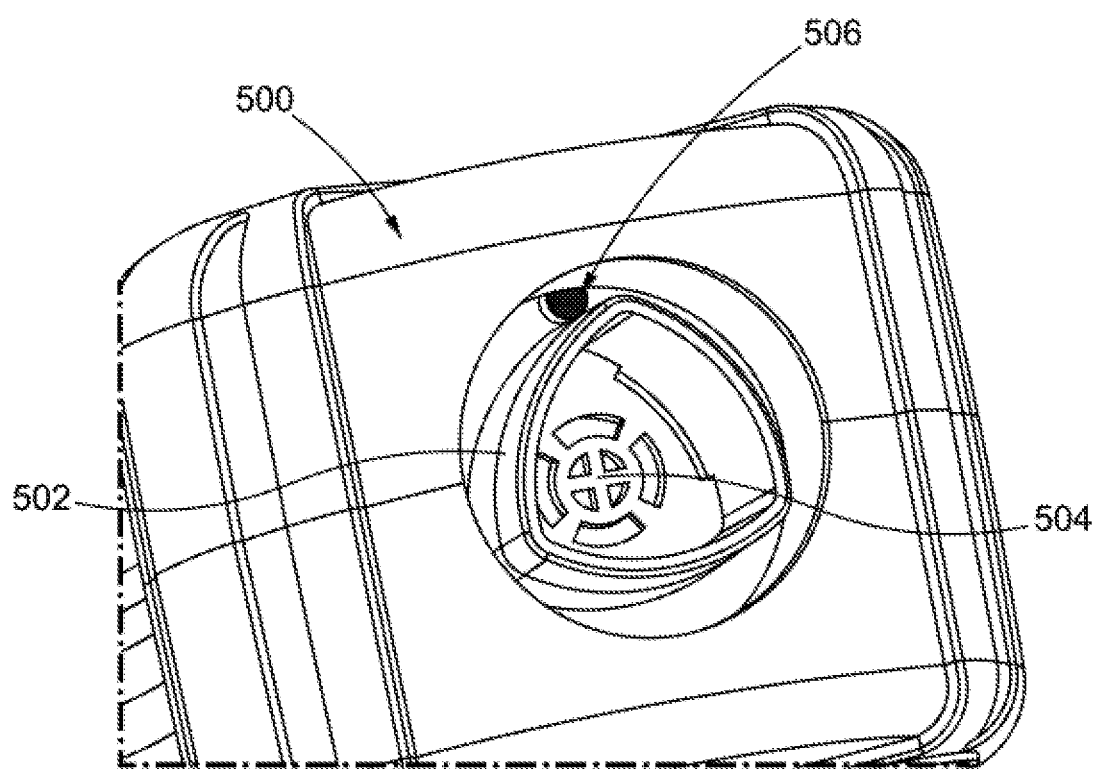
FIG. 5 illustrates an ozone gas release port design of a portable ozone generating device, according to an exemplary aspect.

Referring now to FIG. 4(d), according to another aspect of the present application, the first port 402 of the portal 106 may be a lengthened (e.g., 27.3 mm) and tapered (either in a gradual or stepped manner) hose thereby eliminating the need for multiple connectors and adaptors that are typically required for connecting hoses with different diametrical sizes. It is known that a tubing or hose of a conventional CPAP machine may include either a single large diameter length of tubing or hose running from a pump to a CPAP facemask, or a relatively large diameter length of tubing or hose running from the pump to a combination swivel coupling and reducer fitting located about 18 to 24 inches away from the CPAP facemask, where tubing or hose diameter is reduced to provide a more flexible length of tubing or hose leading to the mask that still is able to provide adequate air flow and pressure. For CPAP user that experience nasal congestion and dryness, heated CPAP tubing may be designed to maintain the temperature of humidified air as it passes through CPAP tube into the facemask. Such heated tubing may be configured to control humidification of generated air flow in real-time based on changes in surrounding environment, such as increases or decreases in temperature or humidity, and changes in CPAP pressure and mask leak. Unlike standard CPAP tubing that has an inside diameter of 19 mm and a 22 mm connection cuff, heated CPAP tubing may use slim or thin flexible tubing with an inside diameter of 15 mm car less. In order to accommodate both heated and conventional CPAP hoses, the embodiment shown in FIG. 4(d) provides a lengthened and tapered cylindrical port 402 which progressively and continuously increases the diameter and wall thickness towards the connector portion 406. Specifically, the port 402 may have a plurality of portions, regions or reaches thereon (e.g., ranging from 14.2 mm or so to 23.6 mm or so) for connecting with heated and conventional CPAP hoses that are different in diametrical sizes and characteristics such as hose thickness, hose strength, hose stiffness, hose flexibility, hose weight, or other characteristics that may be progressively changed along the length of a hose. In one aspect, the plurality of portions, regions or reaches of port 402 may be configured to have surface friction in order to provide different coupling strength, such that disengagement due to pressure change between port 402 and a CPAP hose near the tapered end of port 402 with smaller diameters may be reduced. Further, port 402 may include a plurality of annular grooves along its length for releasably engaging with and retaining CPAP hoses with different diametrical sizes during use.

Similar to the second port 404 described above with respect to FIGS. 4(a)-4(c), the cross-sectional profile of the second port 404 in FIG. 4(d) may be different than that of the first port 402 (e.g., a substantially triangular profile that uniquely mates with a matching port 502 implemented around an ozone gas release port 504 of the ozone generating device 500 as shown in FIG. 5). The second port 404 may be a harder PVC component. The connector portion 406 of FIG. 4(d) may comprise a flange fitted together with a saddle shaped portion. The flange is connected with the first port 402 and the saddle shaped portion is connected with the second port 404.

One of ordinary skill in the art will understand that the aforementioned design of the portal 106 can be accomplished by a wide variety of means and structures. Similarly, the first port 402, the second port 404, and the connector portion 406 may take a wide range of configurations while still enabling the practice of the disclosure.

Further, the sanitizing bag 102 and the portal 106 may be constructed from a variety of materials such as polyethylene, polypropylene, polytetrafluoroethylene, silicone, C-Flex®, ethylene vinyl acetate, chlorinated PVC, polycarbonate, polyvinylidene fluoride (PVDF), etc. These materials may be laminated or co-extruded to provide a bag that has desirable properties such as piercing strength and impact resistance and enclosing ozone gas in an air-tight manner. Further, one or two or more of the following additives may be added within a range or ranges not imparting adverse effects to the performances of the bag 102: a heat stabilizer, an anti-oxidant, a reinforcing material, a pigment, a degradation preventing agent, a weathering agent, a flame retardant, a plasticizer, a preservative agent, an ultraviolet absorber, an anti-static agent and an anti-blocking agent. To improve the slippage of the bag 102, inorganic particles or an organic lubricant may also be added. In addition, the thickness of the bag 102 may be selected based at least on desired mechanical strength and easiness in handling. For example, for small bag design, as the portal 106 may be integrally formed on the bottom end 102d of the bag 102 to serve as an ozone gas conduit between the ozone generating device 104 and other medical device components inside the bag 102, the bottom end 102d may be configured to have a greater thickness than that of, e.g., the side panels of the bag 102. Generally, the thickness of the bag may range from 22 mm to 30 mm.

As further shown in FIG. 1, an active charcoal filter 112 may be placed inside the bag 102 for collecting, breaking down, and releasing remaining ozone as oxygen $O_2$ that can be safely released into the ambient environment via a port. Such charcoal filter 112 may be disposable and changeable after certain usage. Moreover, the lag 102 may have an air pressure release valve 110 installed in the bag 102, e.g, positioned near the top end 102c for detecting and controlling the air pressure of the ozone gas inside the bag 102 during operation. In an alternative design, the active charcoal filter 112, a more rounded, less porous and more dense filter. may be configured to fit behind a flat disc shaped port equipped with an automatic pressure sensitive valve, such that no human intervention is needed to open and release the ozone gas inside the bag 102. The pressure sensitive valve may automatically adjust the air pressure inside an enclosed bag 102 against at least one selected threshold pressure value. For example, the valve may include an opening that automatically decreases in size or closes, in response to detecting the pressure inside the bag 102 is less than the threshold pressure. Moreover, the valve may be configured to maintain a pressure inside the bag 102 during an ozone cleaning cycle. As such, the bag 102 remains inflated but not overly inflated and the contents inside the bag 102 are fully exposed to the ozone gas delivered into the bag 102 for sanitizing purposes. In another example, a collapsible or foldable structure may be placed inside the bag 102 to maintain the bag 102 in an appropriate inflated state during an ozone cleaning cycle.

Figure 6:
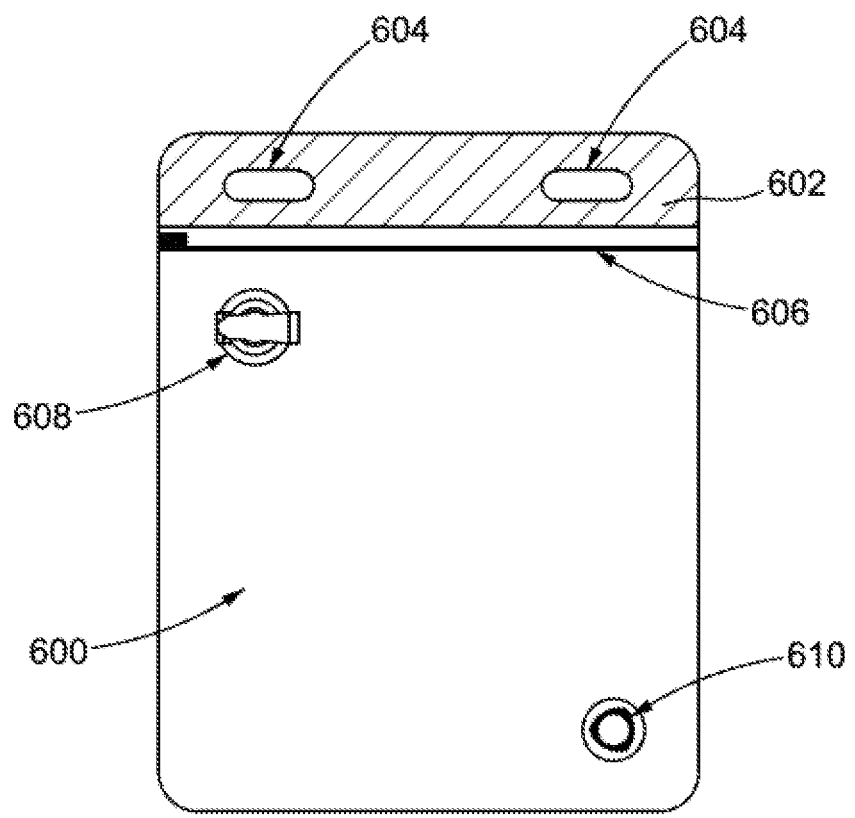
FIG. 6 illustrates another sanitizing bag design, according to an exemplary aspect.

Referring now to FIG. 6, in accordance with another aspect of the present application, a large sized gusset bag 600 may be provided to sanitize a larger quantity of various medical device components and parts using ozone gas. Such bag 600 may include a suspension support panel 602 extending beyond a top sealable end of the bag 600. Support panel 602 may be made of materials that provide rigidity or resistance to bending or tearing and may have multiple hanging holes 604 positioned thereon to allow a user to hang the bag 600 substantially vertically on e.g., nails or hooks on a wall. Generally, the bag 600 may include a number of inventive features similar to the aspects disclosed above with respect to the bag 102 of FIG. 1. For example, the large gusset bag 600 may similarly have two side panels defining a bag interior, a resealable locking means 606 at the top end of the bag, and an air pressure release valve 608 installed and positioned on the bag, e.g., near the top end, and an active charcoal filter placed inside the bag. A portal 610, which is structurally similar to the portal 106 disclosed above, may be positioned on the bag 600, e.g., near the bottom end of the bag 600.

It should be appreciated that the size of the gusset bag may be configured to accommodate various cleaning, disinfecting and sterilizing applications or processes. That is, the portable system disclosed herein may be used to effectively sanitize any consumer goods based on a sizeable bag design. For example, referring to FIGS. 1, 3 and 6, the flexible gusset bag 102 or 600 may be designed in an appropriate shape and size for containing any consumer goods including but not limited to hunting gear, athletic garments and equipment, baby bottles, pacifiers, hotel remote controls, hotel pillows and towels, baby toys, sex toys, dental products (e.g., oral guards, toothbrushes, retainers and dentures), or food items, such that the portable ozone generating device 104 may be configured to deliver generated ozone gas into the interior of the bag for effectively deodorizing, disinfecting, and destroying bacteria, mold, fungi, allergens, and odor-causing agents.

Figure 7:
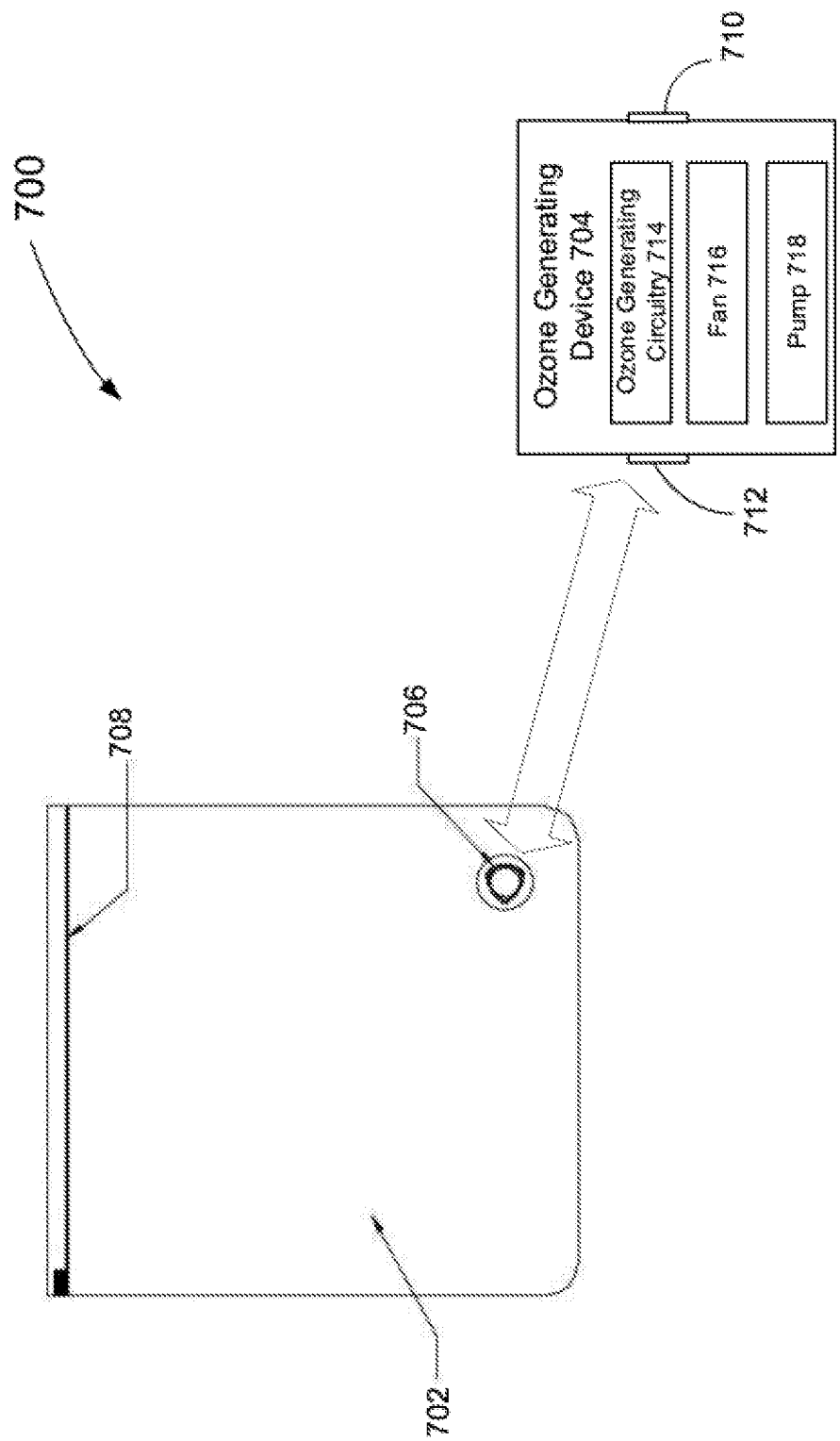
FIG. 7 illustrates an example sanitizing system using ozone gas, according to an exemplary aspect.

Referring now to FIG. 7, according to aspects of the present disclosure, an example sanitizing system 700 using ozone gas may comprise a reusable and disposable vessel 702 connected with an ozone generating device 704 through a portal 706. Similar to aforementioned gusset bag 102, the vessel 702 may be flexible or rigid depending upon the specific usage. "Vessel" here generally includes any structures that may be configured to house objects and fluids (e.g., gas or liquid). It should be appreciated that the vessel 702 may be configured to accommodate various cleaning, disinfecting and sterilizing applications or processes. For example, the vessel 702, flexible or rigid, may be designed in an appropriate shape and size for containing any consumer goods including but not limited to hunting gear, athletic garments and equipment, baby bottles, pacifiers, hotel remote controls, hotel pillows and towels, baby toys, adult sexual devices, dental products (e.g., oral guards, toothbrushes, retainers and dentures), or food items. The ozone generating device 704 may be configured to deliver generated ozone gas into the interior of the vessel 702 for effectively deodorizing, disinfecting, and destroying bacteria, mold, fungi, allergens, and odor-causing agents. A resealable locking means 708 may be provided on one end of the vessel 702 for providing access to the interior of the vessel 702 in an open position and preventing ozone gas leakage in a closed position.

Ozone generating device 704 may be a compact, portable, and rechargeable device configured to generate a safe amount of ozone gas in compliance with relevant government regulations for sanitizing various objects in the vessel 702. In one aspect, ozone generating device may have an inlet port 710 and an outlet port 712 for delivering ozone gas and connecting with various components and devices, as will be described fully below. The outer casing of ozone generating device 704 may be configured to have a figure "8" shape: an asymmetrical figure "8" shape with a small circle and a big circle, or a symmetrical figure "8" shape with two identical sized circles, similar to FIGS. 2(a) and 2(b) illustrated above. In one embodiment, on the top surface of the outer casing, a power button and a liquid crystal display (LCD) may be implemented. A plurality of indicators and signals may be used to display the operating status of ozone generating device 704 to a user via the LCD. Inside the outer casing, ozone gas may be produced via ozone generating circuitry 714 (e.g., a corona discharge or any other suitable technologies), such that oxygen in the air is broken down to charged oxygen atoms which recombine to form molecules of ozone that contain three atoms of oxygen. Moreover, ozone generating device 704 may include circuitry to control a motor of a fan 716 or air pump 718 without generating excessive acoustic noise. Fan 716 here may broadly include any apparatus or device (e.g., impeller or pump) configured to create air pressure difference inside the ozone generating device 704 in order to promote ozone recirculation. For example, such circuitry may be configured to provide speed control to the motor of the fan 716 and the air pump 718 with several selectable impedances. These impedances, typically capacitors, may represent a series of reduced levels of smooth (not switched) power to the motor from a power source of ozone generating device 704 (e.g., battery powered or an AC power source), such that the power reduction in the motor is proportional to the series of impedances. In one aspect, as will be described fully below, at least ozone generating circuitry 714 and fan 716 of ozone generating device 104 may be controlled independent of each other at different stages of an ozone sanitizing cycle.

When one or more items are placed and sealed inside the vessel 702 for sanitizing purposes, ozone generating device 704 may be connected directly with the vessel 702 through its outlet port 712 and the portal 706 before delivering ozone gas into the interior of the vessel 702. The portal 706 may be positioned anywhere on the vessel 702 and may be implemented using a wide variety of means of structures. In the alternative to a direct connection, the ozone generating device 704 may be connected to the vessel 702 using designs shown in FIGS. 4(a)-4(d). For example, portal 706 may include port 402 configured for connecting with an object (e.g., a CPAP hose or facemask, or medical devices with surface irregularity or complexity) placed inside the vessel 702 or simply directing ozone gas into the vessel 702. Portal 706 may include port 404 protruding at the base end of the vessel 702 and used for connecting with the ozone generating device 704 via a matching port thereof (e.g., port 502 of FIG. 5) and receiving ozone gas therefrom. Ports 402 and 404 may have different cross-sectional profiles. In addition, portal 706 may include connector portion 406 used for securely affixing the portal 706 onto a selected position on the vessel 702 and connecting ports 402, 404. As the vessel 702 is designed to be used multiple times, the connector portion 406 should be made of materials that are durable yet flexible with sufficient elastic memory to quickly reposition itself on the vessel 702 in order to maintain air-tight sealing even after repeated insertion and removal of various components on both ports 402 and 404.

As described above, ozone is a strong oxidant and is effective for destroying bacteria, mold, fungi, allergens, odor-causing agents, and pathogens. Various studies have shown that ozone concentration is important to the killing of pathogens on the item being sanitized. Ozone concentration may be commonly measured using parts per million (ppm) which indicates how many parts of the gas in question are in every 1 million parts of total gas. It may be evident that the sanitizing system 700 described herein may limit the ozone concentration in the vessel 702 to the concentration at the output side of ozone generating device 704 if the air/ozone mixture in the vessel 702 is continuously discharged from the vessel 702 to the surrounding environment during a sanitizing cycle. When a relatively high ozone concertation output is desired, the ozone generating device 704 may demand high power consumption. Alternatively, if power is supplied by a battery. the number of ozone cleaning cycles of the sanitizing system 700 may be limited. However, for a rechargeable device, high power consumption may require a high capacity battery, which may lead to a heavier and bulkier design for the ozone gas generator 704.

According to aspects of the present disclosure, as shown in FIGS. 8-19, by at least recirculating the air/ozone mixture in the vessel 702 and ozone generating device 704, the ozone concentration may be increased without requiring an ozone generator have a higher output.

Referring now to FIG. 8, a sanitizing system 800 using ozone gas may comprise a vessel 802 releaseably coupled with an ozone generating device 804 via a suitable connecting means (e.g., hoses or tubes 806 and 808). Vessel 802, similar to the reusable and disposable vessel 102 in FIG. 1, may be flexible or rigid and designed in an appropriate shape and size for containing any consumer goods to be sanitized. A resealable locking means 810 (e.g., a double zipper lock or an interlocking rib-type seal, or other closure means such as plastic or paper-clad-wire ties that have strong resistance to oxidization and corrosion) may be provided on one end of the vessel 802 for providing access to the interior of the vessel 802 in an open position and preventing ozone gas leakage in a closed position.

Ozone generating device 804, similar to the ozone generating device 704 in FIG. 7, may be configured to use various circuitries to generate and deliver an amount of ozone gas via an ozone gas release port 812 at its output end via a connecting hose 806 and an inlet port 814 implemented on vessel 802 into the interior of vessel 802 during operation (ozone gas flow path is represented by an arrow). For example, if portal design 706 is similarly implemented in system 800, each of input and output ports of the connecting hose 806 may be configured to have a profile and configuration complementary to that of the ozone gas release port 812 of ozone generating device 804 and the inlet port 814 of vessel 802, thereby preventing a user from misusing the ozone gas generating device 804 for inappropriate purposes or applications. Furthermore, vessel 802 may be configured to have a recirculation port 816 that is implemented on a selected position on vessel 802 and releasably coupled with a suitable connection means (e.g., hose 808) for directing the air/ozone mixture in the vessel 802 back into the ozone generating device 804 via port 818 at its input end. It should be appreciated that connecting means 806 and 808 may be flexible or rigid and made of materials that have strong resistance to oxidization and corrosion. In one aspect, hoses 806 and 808 may be configured to fit with one or more branch hoses, couplers, or any other connecting apparatus to achieve a desired length. Further, hoses 806 and 808 may be configured to limit or permit longitudinal and rotation movement of various corresponding connecting portions when ozone gas flows therethrough.

Once properly connected with the vessel 802 and powered up, the fan or air pump (not shown) inside the ozone generating device 804 may start drawing in air through a corona discharge to produce ozone gas for, e.g., 5 minutes. When ozone gas flows through ports and hose 812, 806 and 814 into the vessel 802 which is sealed and has one or more items contained therein, sanitizing of the items therein may be carried out as the concentration of ozone gas increases. Due to an air pressure difference generated between the inlet port 814 and recirculation port 816 of vessel 802, as well as the reduced pressure at the inlet side of the fan or air pump, a mixture of ozone and air inside vessel 802 may be driven through ports 816, 818 and hose 808 (gas flow path is represented by an arrow) back into the input end of ozone generating device 804. Relative positions of ports 814 and 816 on vessel 802 may be configured to achieve a selected air pressure difference and circulation rate in connection with the output power of the fan or pump of ozone generating device 804. Thereafter, the ozone gas production may be reduced, stopped, or continued on an intermittent basis.

Figure 11:
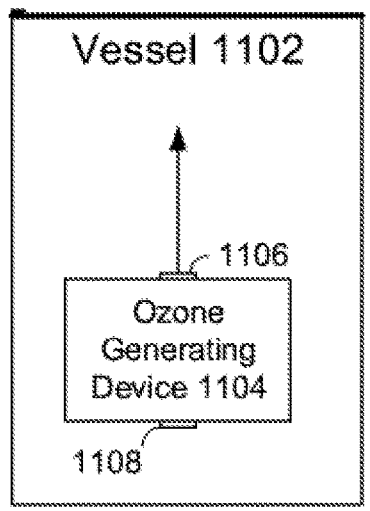
FIG. 11 illustrates a fourth embodiment of recirculating ozone gas within an ozone sanitizing system, according to an exemplary aspect.

It should be appreciated that the ozone recirculation system 800 described above with respect to FIG. 8 may be subjected to various modifications, depending upon, e.g., ozone treatment duration and workload of each specific sanitizing application or process, In an alternative embodiment, as shown in FIG. 9, vessel 902 may be directly coupled with the ozone generating device 904 during operation without using any connecting means, e.g., hose 806 illustrated in FIG. 8. For example, portal design 706 of FIG. 7 may he similarly implemented, such that an inlet port 906 of vessel 902 and an outlet port 908 of ozone generating device 904 may securely connect with each other. In yet another alternative embodiment, as shown in FIG. 10, direct coupling may be implemented on an outlet port 1010 of vessel 1002 and an inlet port 1012 of ozone generating device 1004 for recirculating ozone. Further, as shown in FIG. 11, ozone gas generating device 1104 may be placed inside vessel 1102 during operation with items that need to be sanitized. During an ozone sanitizing cycle, ozone generating device 1104 may be configured to initially produce and deliver ozone gas into the interior of the sealed vessel 1102 via its outlet port 1106. Thereafter, gas mixture inside vessel 402 may he recirculated via an inlet port 1108 of ozone generating device 1104 for additional ozone production. In one aspect, the ozone generating device 1104 may be configured to include a delay timer to allow a user to activate the device and place the device inside the vessel 1102 before ozone generation commences, and audio and/or visual signals for monitoring and controlling such ozone sanitizing cycle.

Figure 12:
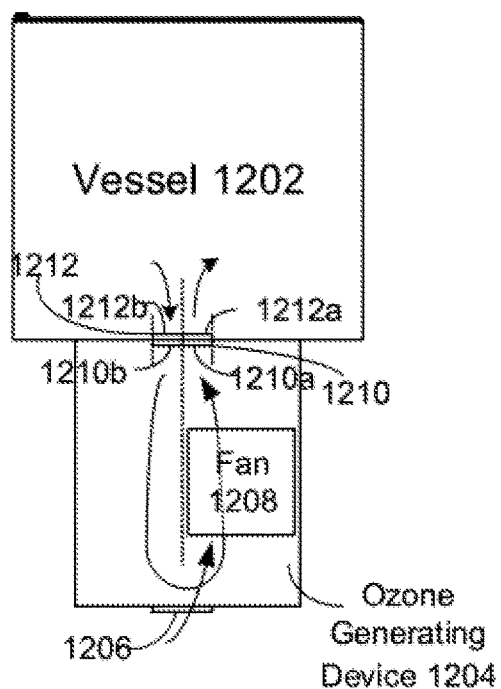
FIG. 12 illustrates a fifth embodiment of recirculating ozone gas within an ozone sanitizing system without using any external connecting tubes or hoses, according to an exemplary aspect.
Figure 13:
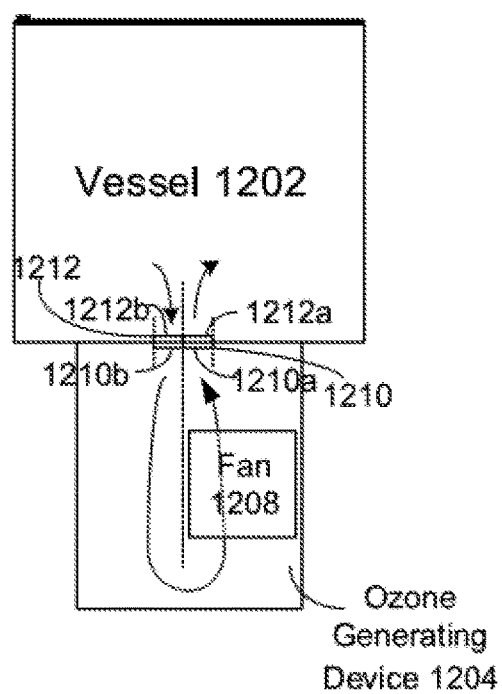
FIG. 13 illustrates a sixth embodiment of recirculating ozone gas within an ozone sanitizing system without using any external connecting tubes or hoses, according to an exemplary aspect.

In another embodiment, as shown in FIGS. 12 and 13, vessel 1202 may be directly coupled with the ozone generating device 1204 during operation without using any external connecting means such a hose or tube. Flow dividing or separation means may be implemented inside ozone generating device 1204 and/or on corresponding connecting ports of vessel 1202 and ozone generating device 1204. Specifically, ozone generating device 1204 may be configured to internally handle multiple gas flow paths and coordinate and direct them to form a circulation and recirculation flow path. For example, air (e.g., either air entering through port 1206 as shown in FIG. 12, or the air inside ozone generating device 1204) may be moved by a fan 1208 through a corona discharge to produce ozone gas and ultimately urged or forced towards an exit port 1210*a* which may be a portion of connecting port 1210 of ozone generating device 1204. Thereafter, ozone gas may flow through an inlet port 1212*a* which is a portion of connecting port 1212 of vessel 1202 and into the interior of vessel 1202. Since ports 1212*b* and 1210*b* of vessel 1202 and ozone generating device 1204 are the only exit openings. the gas mixture may be fed back into ozone generating device 1204, directed internally by fan 1208, and recirculated through the corona discharge of ozone generating device 1204 for additional production of ozone gas. That is, when ozone generating device 1204 is in operation, its fan 1208 or pump may continuously direct either ozone gas or air at a relatively constant velocity through ports 1212*a* and 1210*a*, and a positive pressure difference exists between the opening defined by ports 1212*a* and 1210*a* and the opening defined by ports 1212*b* and 1210*b*. As a result, the gas mixture inside vessel 1202 may be forced through ports 1212*b* and 1210*b* and an effective recirculation thereof may be achieved without using any external hoses or tubes.

To accommodate and direct different gas flow paths, ozone generating device 1204 may be internally configured to have one or more vents, flow dividers, or fans disposed at selected positions along each gas flow path. Further, the connecting ports 1210 and 1212 of ozone generating device 1204 and vessel 1202 may be accomplished using any suitable design so long as generated ozone gas may unrestrictedly flow through a portion of both ports into the interior of vessel 1202 and a return flow passageway is provided for the gas mixture inside vessel 1202 for recirculation with the ozone generating device 1204. In one example, each of ports 1210 and 1212 may be implemented as a unitary body with a divider to separate each opening end into a pair of sub-ports 1210a, 1210b and 1212a, 1212b, respectively. Each pair of sub-ports may have either a symmetrical or asymmetric shape and size. In another example. ports 1210a, 1210b, 1212a, 1212b may be implemented as independent connecting conduits that may be positioned adjacent to one another or near one another.

Figure 14:
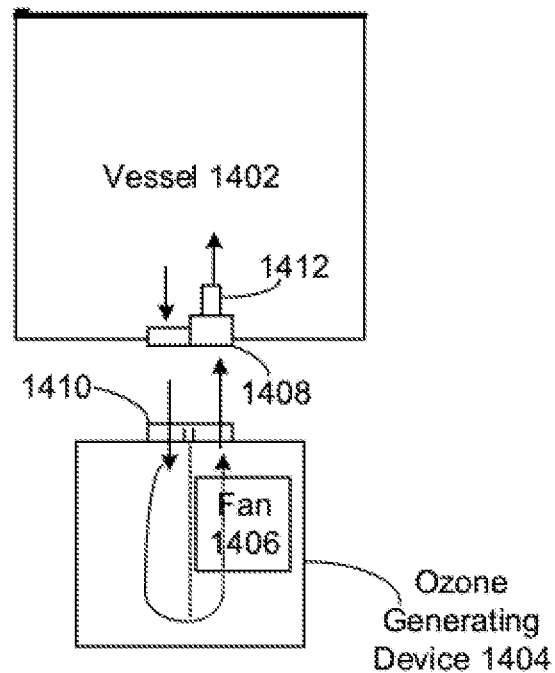
FIG. 14 illustrates a seventh embodiment of recirculating ozone gas within an ozone sanitizing system, according to an exemplary aspect.

As a preferred embodiment for sanitizing CPAP hoses or tubes, referring now to FIG. 14, vessel 1402 may be directly coupled with the ozone generating device 1404 during operation via coupler units 1408 and 1410 without using any external connecting means such as a hose or tube. Similar to aspects described above with respect to FIGS. 12 and 13, each of coupler units 1408 and 1410 may be configured to have at least two sub-ports for delivering ozone gas or air into the interior of vessel 1402 and recirculating gas mixture inside vessel 1402 back to ozone generating device 1404. In one aspect, coupler unit 1408 of vessel 1402 may include a hose connecting portion 1412 which may be detachable from coupler unit 1408. For example. hose connecting portion 1412 may be configured to coaxially receive and tightly engage either an end portion (e.g., 19 mm or so) of a standard CPAP hose directly or a connection cuff of the CPAP hose. In another example, hose connecting portion 1412 may be a lengthened and tapered cylindrical shape including a plurality of portions, regions or reaches thereon (e.g., ranging from 14.2 mm or so to 23.6 mm or so) for connecting with heated and conventional CPAP hoses that are different in diametrical sizes and characteristics such as hose thickness, hose strength, hose stiffness, hose flexibility, hose weight, or other characteristics that may be progressively changed along the length of a hose. Coupler units 1408 and 1410 may be attached to each other via various means (e.g., snap-fit engagement, frictional engagement or any other suitable attachment means).

Figure 15:
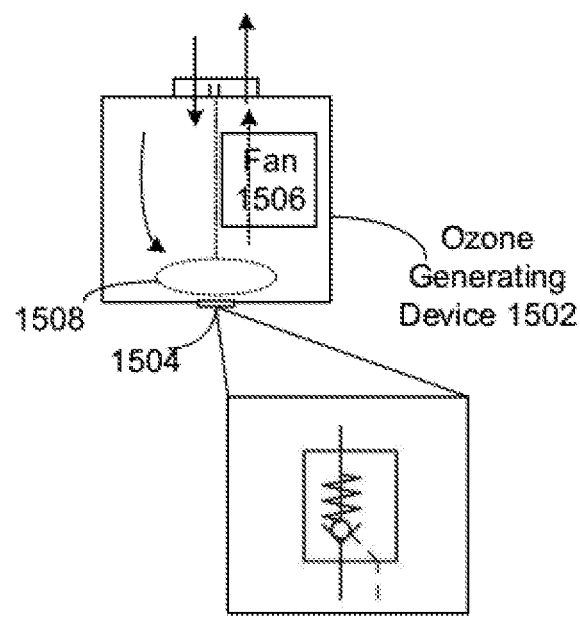
FIG. 15 illustrates an example implementation for inflating a vessel of an ozone sanitizing system at the beginning of an ozone sanitizing cycle, according to an exemplary aspect.

When vessel in FIGS. 8-14 described above is not rigid (e.g., a flexible plastic bag), it may not be inflated initially. However, if one or more top or side panels of a bag are in contact with an item to be disinfected inside the bag, that contact may block ozone gas from treating pathogens in the area of contact. Thus, inflating the bag prior to and/or during an ozone cleaning cycle may improve the efficacy of the system by reducing the contact between the bag and the item being treated. In one embodiment, as shown in FIG. 15, a mechanical check valve 1504 may be coupled with an inlet port of an ozone generating device 1502 where a portion 1508 of the recirculation path inside the ozone generating device 1502 may be configured to produce air pressure difference. It should be appreciated that multiple configurations may be used to produce air pressure difference and one example configuration may involve reducing the cross sectional area in this region 1508 to increase the speed of air/ozone mixture therethrough. When the air/ozone mixture is flowing through this air pressure difference generation region 1508, the pressure inside the region 1508 may be reduced, As a result. ambient air may be continuously drawn in via an inlet port of ozone generating device 1502 until the pressure inside and outside the region 1508 reaches equilibrium. That is, region 1508 may be configured to have fluid communication with the environment surrounding the ozone generating device 1502 via its inlet and outlet ports, such that air may flow into ozone generating device 1502 to compensate the pressure difference inside and outside this region 1508. In the meantime, the internal pressure of a sealed bag (not shown) that is attached to ozone generating device 1502 via its outlet port may gradually increase when air continuously flows in. The bag may be inflated as the air pressure on both side of this region 1508 reaches equilibrium. In one aspect, a check valve 1504 may be configured to allow gas to flow through the inlet port and itself in only one direction and stop backflow. When ozone gas is produced via a corona discharge and moved by a fan 1506 to exit ozone generating device 1502, the cross sectional area in the region 1508 near the check valve 1504 may experience air pressure reduction when a fluid or gas flows through a constricted section (or choke) of a passageway. As a result, check valve 1504 opens when the attached bag is not full due to this effect and closes when the bag is inflated and gas pressure around the check valve reaches equilibrium. It should be appreciated that any suitable type valve may be used, such as a gravity actuated valve, spring loaded valve, or polymer umbrella valve.

Further, due to air pressure difference generated by region 1508, the attached bag may remain inflated and there may be very little exchange of recirculating/air ozone with room air through the inlet port of ozone generating device 1502 when the fan 1506 is running and the internal/external pressure is equalized. As such, check valve 1504 near the region 1508 may not be necessary, so long as the fan 1506 keeps running. In other words, the ozone generating device 1502 may be configured to stop producing ozone gas and no air/ozone may be released if the fan 1506 keeps running.

Figure 16:
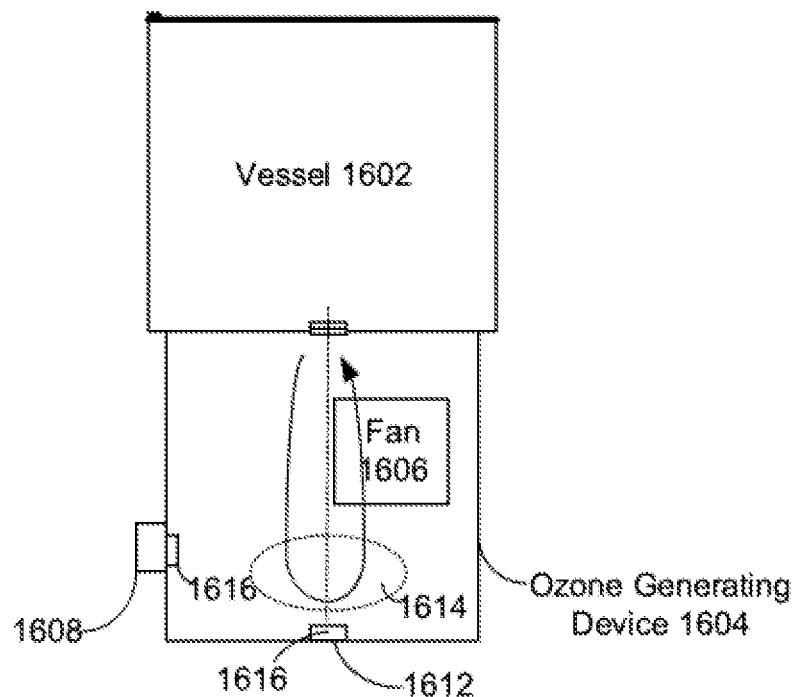
Figure 17:
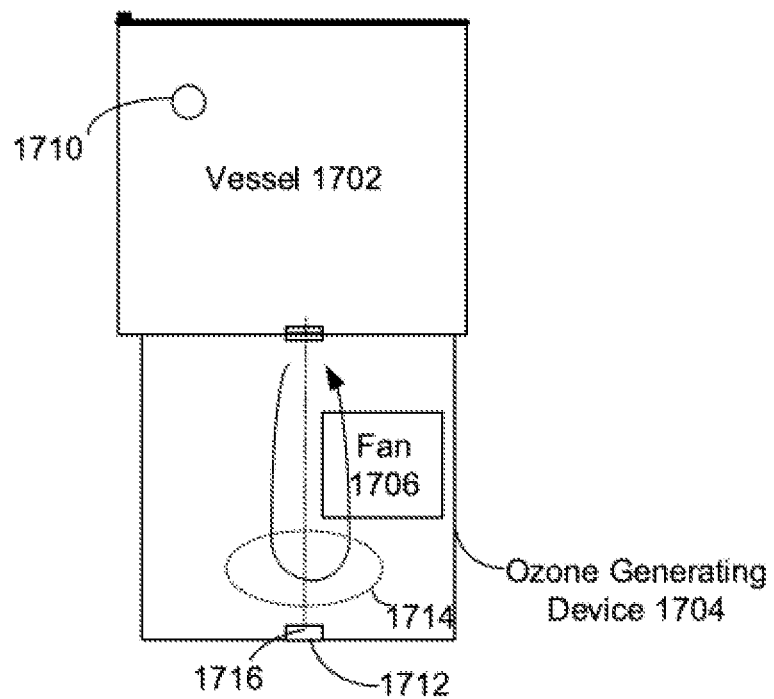

In another embodiment, an actively controlled valve of any suitable type (e.g., microprocessor controlled valves) may be configured to detect signals indicating whether the attached bag is full or inflated to certain extent and remain open to allow air to flow through it until the bag is inflated. For example, such a valve may be configured to be open initially in response to detecting that the fan 1506, but not the ozone generating circuitry, is running, to fill the attached bag. In response to detecting that the ozone generating circuitry has been activated to start producing ozone gas, the valve may be configured to close, FIGS. 16-18 illustrate three example embodiments for purging residual ozone gas within an ozone sanitizing system at the end of an ozone sanitizing cycle. Direct coupling between a vessel and an ozone generating device without using any external connecting tubes or hoses may be implemented, similar to configurations described previously with respect to FIGS. 12 and 13. "Purging" here may broadly refer to any suitable methods for removing, converting or replacing the residual ozone gas of the disclosed ozone sanitizing system. In one aspect, recirculating the ozone gas within the disclosed ozone sanitizing system may be an example purging process or vice versa.

Referring now to FIG. 16, at the end of an ozone sanitizing cycle, to avoid exposing a user or surrounding area to untreated ozone, it may be desirable to purge the ozone inside vessel 1602 and ozone generating device 1604 prior to the vessel 1602 is being opened for retrieval of the contents therein. In accordance with aspects of the present disclosure, such purging may be carried out through an ozone neutralizing device 1608 (e.g., a charcoal filter or other suitable ozone treating device) implemented on ozone generating device 1604. An ozone purge cycle (e.g., a preset amount of time to sufficiently purge the ozone gas) may be employed by activating a fan 1606 (but not the ozone generating circuitry) inside the ozone generating device 1604 to expel the air/ozone mixture through a port equipped with ozone neutralizing device 1608. One or more actively controlled valves 1616 may be installed near discharge ports of the ozone generating device 1604 and near an air pressure difference generation region 1614.

In another aspect, as shown in FIG. 17, purging of residual ozone gas may be carried out through a discharge port 1710 mounted on vessel 1702. Specifically, fan 1706 within the ozone generating device 1704 may be configured to have at least two different speeds (e.g., a lower speed and a higher speed) to passively control a pressure sensitive valve equipped with the discharge port 1710 of vessel 1702 which is similar to the vessel described above with respect to FIGS. 8-14. For example, different fan speeds may be achieved by using a brushless DC motor and using either two different voltages or pulse width modulation. An active charcoal filter may be placed inside the vessel 1702 for collecting, breaking down, and releasing remaining ozone as oxygen $O_2$ that can be safely released into the ambient environment via the discharge port 1710. Such charcoal filter may be disposable and changeable after certain usage. Further, one or more fans 1706 may be implemented inside ozone generating device 1704.

During an ozone generation/sanitation cycle, a lower fan speed may be used to recirculate the air/ozone mixture. As described in FIG. 15, an air pressure difference generation region may be created by constricting/shaping a portion of an air passageway within the ozone generating device. Similarly, as shown in FIGS. 16-18, air may be drawn in through a port 1612, 1712, 1812 near air pressure difference generation region 1614, 1714, 1814 thereby filling a flexible vessel (if a rigid vessel is not used).

During an ozone purge cycle at the end of the ozone generation/sanitation cycle, a higher fan speed may be used to raise the pressure inside vessel (or a rigid chamber), thereby creating a higher pressure difference at the port 1612, 1712, 1812 near air pressure difference generation region 1614, 1714, 1814. A pressure sensitive valve may be incorporated on either the inlet or outlet of the discharge port 1710. The valve may be designed not to open in response to detecting a lower pressure in the vessel when the lower fan speed is running, but configured to open when the fan is running at the higher speed and there is greater pressure in the vessel.

In case of either of the systems depicted in FIGS. 16 and 17, the volume of air/ozone mixture discharged through the discharge ports during the purge cycle is replaced or "made up" inside the system with room air. This may be accomplished using the inlet port connected to air pressure difference generation region 1614, 1714, 1814 as described above, or by using a separate inlet port where air is drawn into the system using a fan or other means for impelling air.

In another aspect, as shown in FIG. 18, ultraviolet (;UV) may be used to decompose ozone. It is known that UV lamps (and other sources of UV) that emit UV light having below 240 nanometers (nm) wavelength can actually generate ozone. However, UV in the range of 250 to 260 nm wavelength may degrade ozone (with a maximum at 254 μm). Accordingly, a UV light generator 1818 may be incorporated into a portion of the recirculation flow path inside the ozone generating device 1804 for purging residual ozone. Specifically, after each sanitation cycle, the UV light emitter or generator may be activated to decompose remaining ozone gas, thereby eliminating the need for a neutralizing device 1608 or discharge port 1710 shown in FIGS. 16 and 17, and creating a completely closed system (unless an inlet port is connected to the air pressure difference generation region as described above, or other means are used, to inflate a flexible vessel before or at the beginning of the sanitizing cycle).

In yet another aspect, one or more flow valves (e.g, valve 1616, 1716, 1816 in FIGS. 16-18), either actively controlled or passively controlled, may be used for purging untreated ozone gas. Such flow valves may generally include any suitable component configured to regulate, direct and control a fluid flow (gases or liquids) by opening, closing, or partially obstructing various passageways. Opening and closing of a passive valve may be controlled by a pressure difference across the valve in the fluid flowing through the valve which is located on each side of the valve. An active valve may be activated or energized by an energy source other than the pressure difference across the valve and may be controllable by a control signal in response to the detection of an elevated or decreased pressure of a fluid flow using any suitable means. For example, such control signal may be generated in response to a signal produced by a pressure sensor when pressure in, e.g., a flow conduit exceeds a predetermined threshold value. An active valve may alternatively be activated by an actuator which generates a control signal for the active valve to close when pressure in, e.g., the vessel. exceeds a predetermined threshold value.

As described previously, air/ozone mixture may be discharged through a port and neutralizing device 1608 on the ozone generating device 1604 which may include media that decomposes ozone. In addition, an actively controlled diverter valve implemented on the ozone generating device may be configured to direct air to the attached sanitizing vessel in one setting, and direct air through a discharge port in another setting. A powered switch may not be required for such valve if passive control thereof may be achieved. For example, using the fan with at least two different speeds described above, the added flow/kinetic energy of the air exiting the fan at the higher speed setting may be used to activate a diverter switch.

Further, one or more actively controlled latches may be incorporated on any discharge port of the ozone generating device or the vessel to prevent accidental release of ozone if the vessel is prematurely disconnected. The ozone generating device may also include a mechanical latch that couples to the zipper (or other means for opening/closing the vessel), such that the mechanical latch remains locked in a closed position (coupled to the zipper) until the sanitation and/or the purge cycle is completed. The mechanical latch may include a sensor configured to detect when the zipper is coupled to the mechanical latch and communicate this information to a system controller, so that the system will not begin the sanitizing cycle until the zipper is detected in the latched position, at which point the lock is engaged.

In accordance with other aspects of the present disclosure, as shown in FIG. 19, coupling structures on vessel 1902 may be configured to indicate vessel sizing information to a connecting ozone generating device 1904, such that different durations of ozone treatment may be determined correspondingly without any input from a user.

For example, vessel 1902 may include a coupling structure 1906 that is configured to uniquely mate with a connecting port 1908 of the ozone generating device 1904, and indicate vessel sizing information to the ozone generating device 1904. That is, specific fixed coupling positions or configurations of structure 1906 may identify the size of the vessel 1902. When connected with each other, the ozone generating device 1904 may automatically detect the coupling positions of 1906 via its contact switches. As illustrated, position "1" on 1906 may be notched so contact switch A is not activated. The remaining position "2" on 1906 may activate contact switch B to indicate a vessel #3 in size 3 is in use, as shown in the following table. Note that "×" indicates a contact switch is activated, it should be appreciated that more positions may be implemented on the coupling structure 1906 and the connecting port 1908. The ozone generating device 1904 may be configured to store an internal look-up table for all possible detection results, and correspondingly determine an appropriate ozone treatment duration based at least on a detected vessel size.

| Detection Result | A | B |
|---|---|---|
| Vessel 1 in size 1 | x | x |
| Vessel 2 in size 2 | x | |
| Vessel 3 in size 3 | | x |
| No Connection (Do Not Start) | | |

Although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise. Thus, the disclosure is not to be limited to the examples and designs described herein but is to be accorded the widest scope consistent with the principles and novel features disclosed herein.

The invention claimed is:

1. A system for sanitizing various objects using ozone gas, the system comprising:
   an ozone generating device comprising:
      an inlet port for at least drawing in ambient air from surrounding environment,
      air moving circuitry implemented inside an outer casing of the ozone generating device configured to propel the ambient air to ozone gas generating circuitry and into a vessel configured to releasably couple with the ozone generating device,
      the ozone gas generating circuitry configured to use the ambient air to generate ozone gas during an ozone sanitizing cycle, and
      an outlet port configured to deliver at least the ozone gas and connect with the vessel; and
   the vessel configured to receive the ozone gas to sanitize one or more objects stored inside the vessel during the ozone sanitizing cycle,
   wherein the vessel comprises:
      a first end having a resealable locking means for providing access to an interior of the vessel in an open position and for enclosing the vessel in a closed position,
      a second end having a portal implemented thereon and configured to form a connection with the outlet port of the ozone generating device, and
      a discharge port for discharging at least the ozone gas inside the vessel,
   wherein the ozone generating device comprises a switch configured to prevent the ozone generating device from producing the ozone gas in response to detecting that the connection between the outlet port of the ozone generating device and the portal of the vessel is improper, thereby preventing ozone gas leakage through the connection,
   wherein, at the end of the ozone sanitizing cycle, the ozone generating device is configured to stop the ozone gas generating circuitry and operate the air moving circuitry for a preset period of time to draw in the ambient air via the inlet port and propel the ambient air through the ozone generating device and the vessel to reduce a concentration of the ozone gas inside the ozone generating device and vessel.

2. The system of claim 1, wherein the resealable locking means comprises at least one of: a zipper, a double zipper lock, an interlocking rib-type seal, and plastic or paper-clad-wire ties.

3. The system of claim 1, wherein the discharge port of the vessel is equipped with an ozone gas neutralizing device.

4. The system of claim 3, wherein the ozone gas neutralizing device comprises at least one charcoal filter.

5. The system of claim 1, wherein the air moving circuitry of the ozone generating device comprises at least one of a fan and air pump.

6. The system of claim 1, wherein the portal of the vessel comprises a first port, a second port for connecting with the outlet port of the ozone generating device, and a connector portion affixing the portal to the second end of the vessel and connecting the first and second ports.

7. The system of claim 1, further comprising a connecting means for coupling the outlet port of the ozone generating device and the portal of the vessel such that at least the ozone gas generated by the ozone generating device is directed into the vessel through the connecting means.

8. The system of claim 1, wherein the ozone gas generating circuitry comprises a corona discharge to generate the ozone gas.

9. The system of claim 1, wherein the vessel is closed during the preset period of time.

10. The system of claim 1, wherein the ozone generating device is portable and rechargeable.

\* \* \* \* \*